United States Patent
Boswell et al.

(10) Patent No.: US 9,486,546 B2
(45) Date of Patent: Nov. 8, 2016

(54) METHODS AND COMPOSITIONS FOR RADIOHALOGEN PROTEIN LABELING

(71) Applicant: Genentech, Inc., South San Francisco, CA (US)

(72) Inventors: Charles Andrew Boswell, Millbrae, CA (US); Leslie A. Khawli, Claremont, CA (US); Jan Marik, Hillsborough, CA (US); Simon Williams, Redwood City, CA (US)

(73) Assignee: GENENTECH, INC., South San Francisco, CA (US)

( * ) Notice: Subject to any disclaimer, the term of this patent is extended or adjusted under 35 U.S.C. 154(b) by 206 days.

(21) Appl. No.: 14/814,734

(22) Filed: Jul. 31, 2015

(65) Prior Publication Data

US 2016/0002121 A1 Jan. 7, 2016

Related U.S. Application Data

(62) Division of application No. 14/132,252, filed on Dec. 18, 2013, now Pat. No. 9,393,327.

(60) Provisional application No. 61/739,249, filed on Dec. 19, 2012.

(51) Int. Cl.

| *A61K 49/16* | (2006.01) |
| *A61K 51/04* | (2006.01) |
| *C07K 16/28* | (2006.01) |
| *C07K 5/02* | (2006.01) |
| *A61K 51/08* | (2006.01) |
| *A61K 51/10* | (2006.01) |
| *C07B 59/00* | (2006.01) |
| *C07D 207/404* | (2006.01) |
| *C07D 207/452* | (2006.01) |

(52) U.S. Cl.
CPC ........... *A61K 49/16* (2013.01); *A61K 51/0482* (2013.01); *A61K 51/088* (2013.01); *A61K 51/103* (2013.01); *A61K 51/1093* (2013.01); *C07B 59/002* (2013.01); *C07D 207/404* (2013.01); *C07D 207/452* (2013.01); *C07K 5/02* (2013.01); *C07K 16/28* (2013.01)

(58) Field of Classification Search
CPC ........ A61K 49/00; A61K 49/16; C07K 1/00; C07K 5/02; C07K 16/02
See application file for complete search history.

(56) References Cited

U.S. PATENT DOCUMENTS

| 7,521,541 B2 | 4/2009 | Eigenbrot et al. |
| 2004/0096394 A1 | 5/2004 | Govindan |
| 2010/0111856 A1 | 5/2010 | Gill |
| 2010/0221176 A1 | 9/2010 | Gill et al. |

OTHER PUBLICATIONS

G. Vidyanathan et al. SIB-DOTA: A trifunctional prosthetic group potentially amenable for multi-modal labeling that enhances tumor uptake of internalizing monoclonal antibodies, Bioorganic & Medicinal Chemsitry, 20, 6929-6939, 2012.*
Adam et al., "Radiohalogens for imaging and therapy", Chem Soc Rev. 34(2);153-63 ( 2005).
Boswell et al. et al., "Development of radioimmunotherapeutic and diagnostic antibodies; an inside-out view" Nucl Med Biol 34:757-778 ( 2007).
Boswell et al., "An integrated approach to identify normal tissue expression of targets for antibody-drug conjugates: case study of TENB2" Br J Pharmacol. 168(2):445-57 ( 2013).
Boswell et al., "Comparative physiology of mice and rats: radiometric measurement of vascular parameters in rodent tissues" Mol Pharm. 11(5):1591-8 ( 2014).
Boswell et al., "Compartmental tissue distribution of antibody therapeutics: experimental approaches and interpretations" AAPS J. 14(3):612-8. ( 2012).
Boswell et al., "Differential effects of predosing on tumor and tissue uptake of an 111In-labeled anti-TENB2 antibody-drug conjugate" J Nucl Med. 53(9):1454-61 ( 2012).
Boswell et al., "Enhanced tumor retention of a radiohalogen label for site-specific modification of antibodies" J Med Chem. 56(23):9418-26 ( 2013).
Boswell et al., "Impact of drug conjugation on pharmacokinetics and tissue distribution of anti-STEAP1 antibody-drug conjugates in rats" Bioconjug Chem. 22(10):1994-2004 ( 2011).
Chen et al., "MicroPET and autoradiographic imaging of breast cancer a $_v$-integrin expression using $^{18}$F- and $^{64}$Cu-labeled RGD peptide" Bioconj Chem 15:41-49 ( 2004).
Chizzonite et al., "IL-12: Monoclonal Antibodies Specific for the 40-kDa Subunit Block Receptor and Biologic Activity on Activated Human Lymphoblasts" J Immunol 147(5):1548-1556 (Sep. 1991).
DeNardo et al., "Are radiometal-labeled antibodies better than iodine-131-labeled antibodies: comparative pharmacokinetics and dosimetry of copper-67-, iodine-131-, and yttrium-90-labeled Lym-1 antibody in patients with non-Hodgkin's lymphoma" Clin Lymphoma 1(2):118-26 ( 2000).

(Continued)

*Primary Examiner* — Michael G Hartley
*Assistant Examiner* — Jagadishwar Samala
(74) *Attorney, Agent, or Firm* — Alex Andrus

(57) ABSTRACT

Methods and compositions are provided for labeling proteins with radiohalogen-label reagents. Radiohalogen-labeled proteins may be used for imaging studies, as therapeutics and in diagnostic tests. The [$^{125}$I] HIP-DOTA label reagent 6 is prepared by an efficient and convenient process.

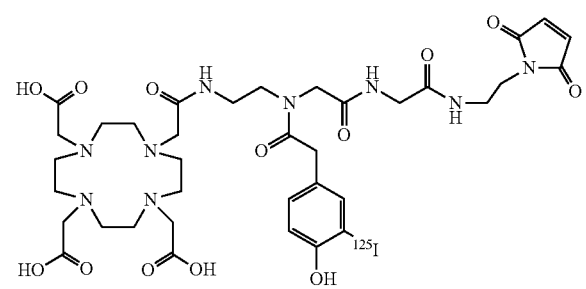

5 Claims, 9 Drawing Sheets

(56) References Cited

OTHER PUBLICATIONS

Govindan et al., "Labeling of monoclonal antibodies with diethylenetriaminepentaacetic acid-appended radioiodinated peptides containing D-amino acids" oconjug Chem. 10(2):231-40 (1999).

Junutula et al., "Rapid identification of reactive cysteine residues for site-specific labeling of antibody-Fabs" J Immunol Methods 332:41-52 (2008).

Junutula et al., "Site-specific conjugation of a cytotoxic drug to an antibody improves the therapeutic index" Nat Biotechnol 26(8):925-32 (Aug. 2008).

Khawli et al., "N-(m-[125I]iodophenyl)maleimide: an agent for high yield radiolabeling of antibodies" Int J Rad Appl Instrum B. 19(3):289-95 (1992).

Khawli et al., "Synthesis of 125I labeled N-succinimidyl p-iodobenzoate for use in radiolabeling antibodies" Int J Rad Appl Instrum B. 16(7):727-33 (1989).

Milenic et al., "Antibody-targeted radiation cancer therapy" Nat Rev Drug Discov. 36:488-99 (2004).

Pastuskovas et al., "Effects of anti-VEGF on pharacokinetics, biodistribution, and tumor penetration of trastuzumab in a preclinical breast cancer model" Mol Cancer Ther. 11(3):752-62 (2012).

PCT ISR for PCT/US2013/075970.

Rogers et al., "Identification of metabolites of 111In-diethylenetriaminepentaacetic acid-monoclonal antibodies and antibody fragments in vivo" Cancer Res. 55:5714s-5720s (1995).

Shankar et al., "N-succinimidyl 3-[(131)I]iodo-4-phosphonomethylbenzoate ([(131)I]SIPMB), a negatively charged substituent-bearing acylation agent for the radioiodination of peptides and mAbs" Bioconjug Chem. 14(2):331-41 (2003).

Sharkey et al., "Advantage of residualizing radiolabels for an internalizing antibody against the B-cell lymphoma antigen, CD22" Cancer Immunol Immunother. 44(3):179-88 (1997).

Shen et al., "Conjugation site modulates the in vivo stability and therapeutic activity of antibody-drug conjugates" Nature Biotechnology 30(2):184-190 (Feb. 2012).

Shih et al., "The processing and fate of antibodies and their radiolabels bound to the surface of tumor cells in vitro: a comparison of nine radiolabels" J Nucl Med. 35(5):899-908 (1994).

Stein et al., "Advantage of a residualizing iodine radiolabel in the therapy of a colon cancer xenograft targeted with an anticarcinoembtryonic antigen monoclonal antibody" Clin Cancer Res. 11(7):2727-34 (2005).

Thorpe et al., "The design and application of residualizing labels for studies of protein catabolism" FASEB J. 7(5):399-405 (1993).

Tolmachev et al., "Approaches to improve cellular retention of radiohalogen labels delivered by internalising tumour-targeting proteins and peptides" Curr Med Chem. 10(22):2447-60 (2003).

Vaidyanathan et al., "Evaluation of an anti-p185(HER2) (scFv-C(H)2-C(H)3)2 fragment following radioiodination using two different residualizing labels: SGMIB and IB-Mal-D-GEEEK" Nucl Med Biol. 36(6):671-80 (2009).

Vaidyanathan et al., "SIB-DOTA: a trifunctional prosthetic group potentially amenable for multi-modal labeling that enhances tumor uptake of internalizing monoclonal antibodies" Bioorg Med Chem. 20(24):6929-39 (2012).

Vaidyanathan, "A polar substituent-containing acylation agent for the radioiodination of internalizing monoclonal antibodies: N-succinimidyl 4-guanidinomethyl-3-[131I]iodobenzoate ([131I]SGMIB)" Bioconjug Chem. 12(3):428-38 (2001).

Wilbur, "Radiohalogenation of proteins: an overview of radionuclides, labeling methods, and reagents for conjugate labeling" Bioconjug Chem. 3(6):433-70 (1992).

Williams, "Tissue distribution studies of protein therapeutics using molecular probes: molecular imaging" AAPS J. 14(3):389-99 (2012).

Zalutsky et al., "Radiohalogenation of a monoclonal antibody using an N-succinimidyl 3-(tri-n-butylstannyl)benzoate intermediate" Cancer Res. 48(6):1446-50 (1988).

\* cited by examiner

METHODS AND COMPOSITIONS FOR RADIOHALOGEN PROTEIN LABELING

CROSS REFERENCE TO RELATED APPLICATIONS

This divisional application filed under 37 CFR §1.53(b) of U.S. Ser. No. 14/132,252, filed 18 Dec. 2013, claims the benefit under 35 USC §119(e) of U.S. Provisional Application Ser. No. 61/739,249 filed on 19 Dec. 2012, which is incorporated by reference in their entirety.

FIELD OF THE INVENTION

The invention relates generally to methods to conjugate or label groups to proteins. The invention also relates to labeled proteins, and intermediates and reagents useful to prepare radiolabeled proteins for research and clinical development of novel therapeutics and diagnostic tests.

BACKGROUND

A known limitation of iodine radionuclides for labeling and biological tracking of receptor targeted proteins is the tendency of iodotyrosine to rapidly diffuse from cells following endocytosis and lysosomal degradation. In contrast, radiometal-chelate complexes such as indium-111-1,4,7,10-tetraazacyclododecane-1,4,7,10-tetraacetic acid ($^{111}$In-DOTA) accumulate within target cells due to the residualizing properties of the polar, charged metal-chelate-amino acid adduct. Iodine radionuclides boast a diversity of nuclear properties and chemical means for incorporation, prompting efforts to covalently link radioiodine with residualizing molecules.

The antigen specificity of monoclonal antibodies is a powerful attribute that allows the site-specific in vivo delivery of payloads, including chemotherapeutic drugs and radionuclides (Wu, A. M.; Senter, P. D. (2005) *Nat Biotechnol.*, 23:1137). To date, only two radioimmunotherapeutic agents have received marketing approval, and both feature murine monoclonal antibodies targeting the CD20 receptor for treatment of lymphoma (Boswell, C. A., et al (2007) *Nucl Med Biol,* 34:757). BEXXAR® (tositumomab) incorporates the β-emitting iodine radionuclide, $^{131}$I, attached via tyrosine residues. ZEVALIN® (ibritumomab tiuxetan) is administered with the β-emitting yttrium radionuclide, $^{90}$Y, attached via tiuxetan, an analog of diethylenetriamine pentaacetic acid (DTPA), through lysine residues. This labeling strategy is analogous to the complexation of the indium radionuclide, $^{111}$In, by 1,4,7,10-tetraazacyclododecane-1,4,7,10-tetraacetic acid (DOTA). Various methods of radiolabeling antibodies are known, including: (A) non-residualizing, oxidative radioiodination of tyrosines, (B) residualizing, lysine modification with radiometal chelate, (C) residualizing, lysine modification with charged iodinated groups (Vaidyanathan, G.; et al, (2001) *Bioconjug Chem.,* 12:428; Shankar, S. et al, (2003) *Bioconjug Chem.,* 14:331), and (D) lysine modification with DOTA-SIB (Vaidyanathan et al (2012) Bioorg. & Med. Chem. 20:6929-6939).

Beyond their clinical utility, radioimmunoconjugates are also useful as tools in translational research for studying conventional, non-radioactive antibody therapeutics (Boswell, C. A., et al (2012) *Aaps J.,* 14:612). Confirmation of target localization, screening for off-target uptake, and receptor occupancy studies (by means of dose escalation) may all be facilitated by the use of radiolabeled antibodies. The available in vivo modalities include non-invasive small animal imaging, whole-body autoradiography, and invasive biodistribution studies. In addition to $^{131}$I, $^{125}$I is commonly used for such studies, with the latter having the advantages of a roughly tenfold lower γ (gamma) energy, the absence of a β (beta) particle emission, and a much longer decay half-life (Wilbur, D. S. (1992) *Bioconjug Chem,* 3:433). See Table 1. Single photon emission computed tomography (SPECT) imaging may be performed with $^{123}$I, $^{131}$I, and $^{125}$I, the latter being limited to preclinical small animal cameras. Positron emission tomography (PET) with $^{124}$I is also feasible, although the highly energetic emissions limit the image quality (Williams, S. P. (2012) *AAPS J.* 14(3): 389-99. doi: 10.1208/s12248-012-9348-3. Epub 2012 Mar. 31.

Tissue distribution studies of protein therapeutics can be conducted using molecular probes and molecular imaging.

Labeling of antibodies with radiometals results in a different cellular distribution of radioactivity relative to traditional tyrosine-based radiohalogenation (Shih, L. B., et al (1994) *J Nucl Med,* 35:899). For both labeling methods, antibodies undergo receptor-mediated endocytosis and lysosomal degradation. However, cellular efflux of the radiolabel with its covalently associated amino acid does not occur for radiometal-labeled antibodies, see FIGS. 1A and 1B (Rogers, B. E., et al (1995) *Cancer Res.,* 55:5714s; Vaidyanathan et al (2012) *Bioorg. & Med. Chem.* 20:6929-6939). Antibodies labeled with $^{125}$I through tyrosine residues undergo (1) receptor-mediated endocytosis, (2) lysosomal degradation and (3) diffusion of [$^{125}$I]-iodotyrosine out of the cell. Steps (1) and (2) also occur for antibodies labeled with $^{111}$In-DOTA through lysine residues; however, step (3) is greatly diminished due to the poor membrane diffusion of the radiolabeled catabolite, $^{111}$In-DOTA-lysine. Unlike [$^{125}$I]-iodotyrosine, which diffuses out of the cell following proteolysis, In-DOTA-lysine is too charged and polar to easily cross the plasma membrane and is therefore intracellularly trapped and referred to as a residualizing label. The relatively short decay half-life of 2.8 days for $^{111}$In makes long-term preclinical studies problematic particularly for labeled antibodies with pharmacokinetic half-lives on the order of 1-2 weeks. Another consideration is that the γ energy of $^{125}$I is nearly ten-fold lower relative to $^{111}$In, with lower energy emissions often associated with superior autoradiographic image quality and lower radiation exposure to workers. A residualizing iodine probe would combine the long decay half-life and low energy of $^{125}$I with the superior tumor accretion of radiometals, while providing a facile translational route to clinical imaging via $^{123}$I or $^{124}$I, or radioimmunotherapy via $^{131}$I (Milenic et al (2004) Nat. Rev. Drug Discov. 3:488-499).

TABLE 1

Overview of common halogen radionuclides.

| Nuclide | Emission[†] (Energy, keV) | Physical Decay $t_{1/2}$ (d) | Diagnostic and/or Therapeutic Uses |
| --- | --- | --- | --- |
| $^{123}$I | γ (159) | 0.5 | SPECT imaging |
| $^{124}$I | γ (603), β$^+$ (831) | 4.2 | PET imaging |
| $^{125}$I | γ (35) | 60 | preclinical SPECT |
| $^{131}$I | γ (365), β$^-$ (182) | 8.0 | radioimmunotherapy, SPECT |
| $^{211}$At | α (5867), γ (687) | 0.3 | radioimmunotherapy |

[†]Values correspond to the most abundant γ emissions and the mean α/β energies, respectively.

Significant effort has been made to derive strategies for labeling antibodies with iodine such that residualization occurs in a similar manner as for radiometals. This reflects, in part, the wide availability of iodine radionuclides with diverse nuclear properties, in terms of both decay half-lives and energies (Table 1), and an abundant knowledge of halogen radiochemistry (Wilbur, D. S. (1992) *Bioconjug Chem*, 3:433). To date, strategies used to achieve this goal include the use of various combinations of (i) nonmetabolizable carbohydrates, (ii) nonmetabolizable peptide adducts, and/or (iii) synthetically derived molecules containing charged moieties. The carbohydrate derivative dilactitol-$^{125}$I-tyramine is a member of the (i) first class of residualizing radioiodine probes (Thorpe, S. R., et al (1993) *Faseb J.*, 7:399). However, the use of carbohydrates may produce unwanted behavior, as pendant sugar groups are important for binding of antibodies to Fc receptors and other critical functions. Representing the (ii) second class is the residualizing peptide, IMP-R4 (MCC-Lys(MCC)-Lys(X)-D-Tyr-D-Lys(X)-OH, where MCC is 4-(N-maleimidomethyl)-cyclohexane-1-carbonyl and X is 1-((4-thiocarbonylamino)benzyl)-DTPA (Stein, R., et al (2003) *Cancer Res.*, 63:111). This approach relies on a synthetic peptide that is conjugated with the chelate DTPA, whose charge imparts residualizing properties (Govindan, S. V., et al (1999) *Bioconjug Chem.*, 10:231). Examples of the (iii) third class of charged synthetic molecules, many of which involve lengthy synthetic routes, include the use of organostannanes (Vaidyanathan, G., et al (2001) *Bioconjug Chem.*, 12:428; Shankar, S.; Vaidyanathan, G., et al (2003) *Bioconjug Chem*, 14:331; Vaidyanathan et al (2012) Bioorg. & Med. Chem. 20:6929-6939). In this direction, a shelf-stable intermediate compound that is readily attainable via synthetic organic chemistry and avoids the use of peptide or carbohydrate moieties, or lengthy synthetic routes, would be useful for radiohalogen-labeling proteins.

SUMMARY

The invention relates to the synthesis of a 4-hydroxy-3-iodophenyl (HIP) probe 6 using an Ugi multi-component reaction (Ugi, I., et al (1959) *Angewandte Chemie*, 71:386; Domling, A., et al (2000) *Angew Chem Int Ed Engl.*, 39:3168). See FIGS. 2 and 3. The probe was conjugated to an antibody and demonstrated to exhibit superior tumor uptake and retention relative to a conventional tyrosine radioiodinated control antibody. These findings offer a novel method for introducing radiohalogen labels into antibodies and thus may serve as a useful preclinical tool for studying the biodistribution, metabolism, and excretion of antibody therapeutics. Furthermore, antibodies labeled with residualizing radionuclides offer unique advantages as radioimmunotherapeutic agents because they may provide a more sustained retention of radioactivity inside tumor cells (DeNardo, G. L., et al (2000) *Clin Lymphoma*, 1:118). Assuming that efficacy is related to tumor radiation exposure, the use of residualizing radioimmunotherapeutic agents may have the potential to attain high target radiation exposure and favorable clinical responses (Sharkey, R. M., et al (1997) *Cancer Immunol Immunother*, 44:179; Vaidyanathan et al (2012) *Bioorg. & Med. Chem.* 20:6929-6939).

An aspect of the invention is a radiohalogen-labeled protein having the structure:

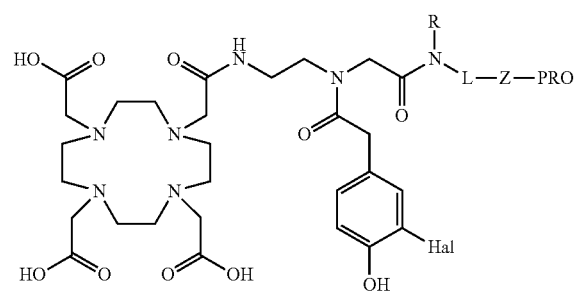

wherein

Hal is a radiohalide isotope selected from $^{123}$I, $^{124}$I, $^{125}$I, $^{131}$I, and $^{211}$At;

L is a linker;

Z is selected from X, S, NH, CH$_2$C(O), C(O), (CH$_2$CH$_2$O)$_n$CH$_2$C(O), NHC(O), NHC(S), OP(O)$_2$, (CH$_2$CH$_2$O)$_n$CH$_2$X, and (C$_1$-C$_{12}$ alkylene)X, where X is

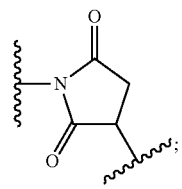 [SMILES: *C1CC(=O)N(*)C1=O]

and

PRO is a protein.

An exemplary embodiment of the invention is a radiohalogen-labeled protein having the structure:

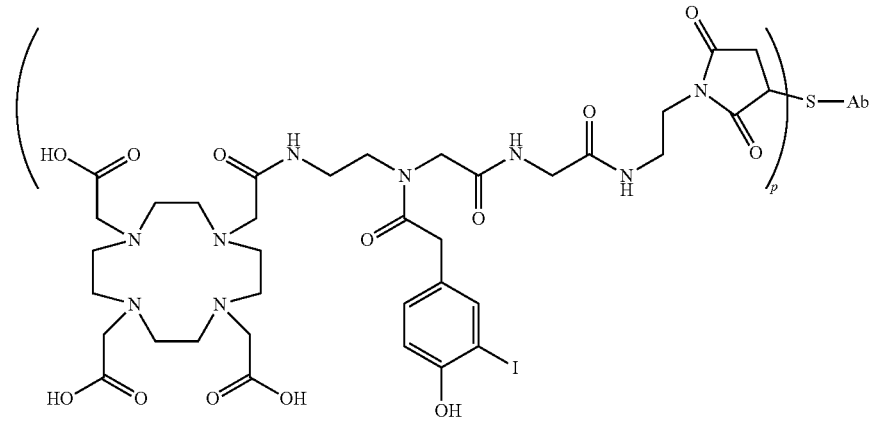

wherein

I is an iodine isotope selected from $^{123}$I, $^{124}$I, $^{125}$I, and $^{131}$I; and Ab is an antibody; and p is about 2.

An aspect of the invention includes methods of labeling a protein comprising reacting a radiohalogen-labeling reagent having the structure:

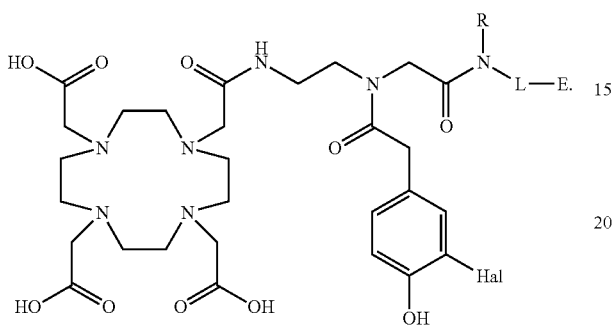

An exemplary embodiment of the invention is the radiohalogen-labeling reagent:

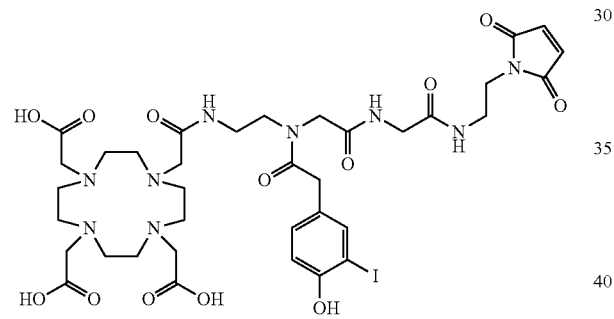

where I is an iodine isotope selected from $^{123}$I, $^{124}$I, $^{125}$I, and $^{131}$I.

An aspect of the invention is a process for preparing a radiohalogen-labeled protein having the structure:

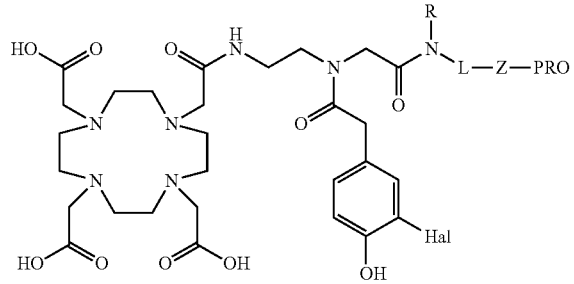

An aspect of the invention includes pharmaceutical compositions of radiohalogen-labeled proteins and one or more pharmaceutically acceptable carrier, glidant, diluent, or excipient.

An aspect of the invention includes methods of imaging comprising: administering a radiohalogen-labeled protein to an animal; and detecting in vivo the presence of the radiohalogen-labeled protein by imaging.

An aspect of the invention is a radiohalogen-labeling reagent having the structure:

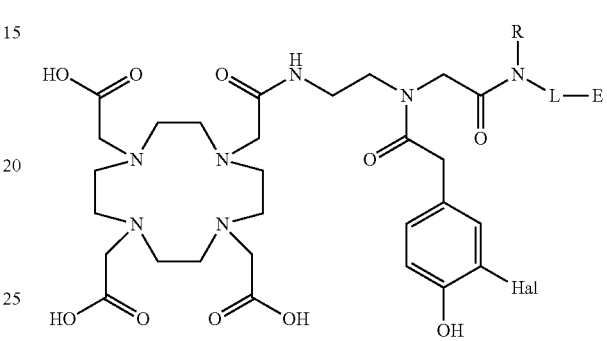

wherein

Hal is a radiohalide isotope selected from $^{123}$I, $^{124}$I, $^{125}$I, $^{131}$I, and $^{211}$At;

L is a linker; and

E is a reactive functional group selected from maleimide, thiol, amino, bromide, bromoacetamido, p-toluenesulfonate, iodide, hydroxyl, carboxyl, aldehyde, pyridyl disulfide, N-hydroxysuccinimide, azido, isocyanato, isothiocyanato, and phosphoramidite.

An aspect of the invention is processes for making a radiohalogen-labeling reagent having the structure:

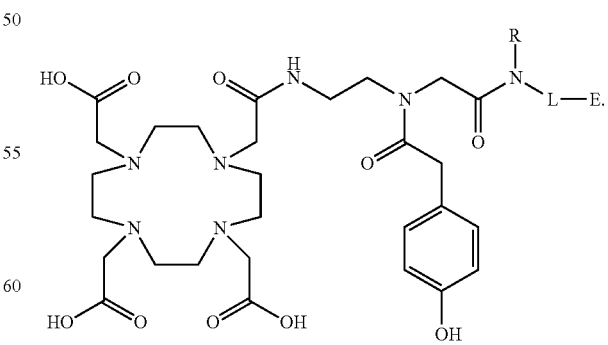

An aspect of the invention is a process for making a radiohalogen-labeling reagent having the structure:

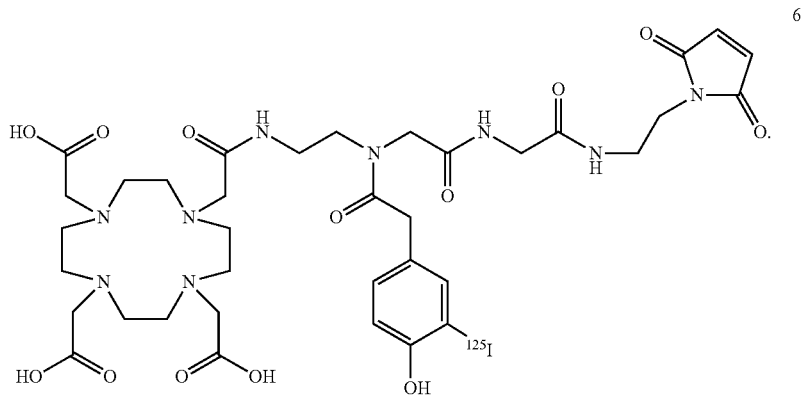 [SMILES: O=C(O)CN1CCN(CC(=O)O)CCN(CC(=O)NCCN(CC(=O)NCC(=O)NCCN2C(=O)C=CC2=O)C(=O)Cc2ccc(O)c([125I])c2)CCN(CC(=O)O)CC1]

DETAILED DESCRIPTION OF THE EXEMPLARY EMBODIMENTS

Figure 1A:
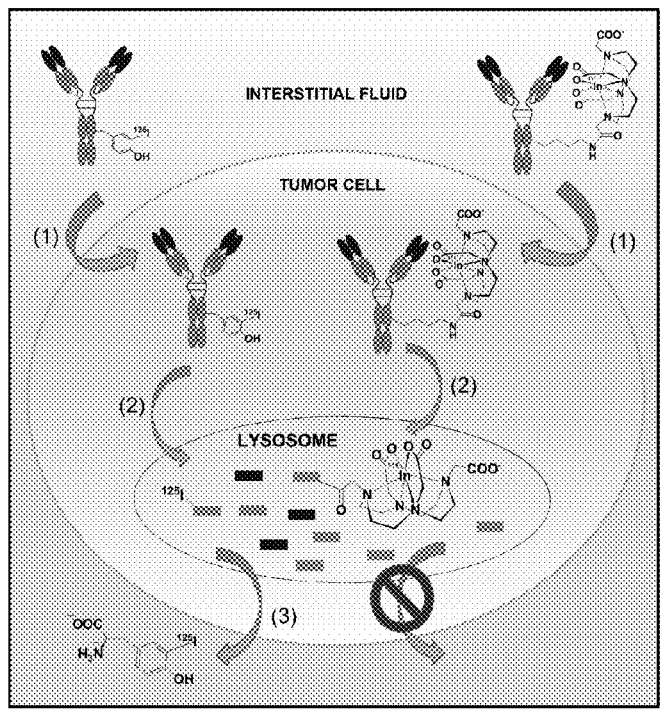
FIGS. 1A and 1B show schematics depicting the cellular fates of non-residualizing and residualizing labels following antibody binding to an internalizing cell-surface antigen. Antibodies labeled with $^{125}$I through tyrosine residues undergo (1) receptor-mediated endocytosis, (2) lysosomal degradation and (3) diffusion of [$^{125}$I]-iodotyrosine out of the cell. Steps (1) and (2) also occur for antibodies labeled with $^{111}$In-DOTA through lysine residues; however, step (3) is greatly diminished due to the poor membrane diffusion of the radiolabeled catabolite, $^{111}$In-DOTA-lysine.
Figure 1B:
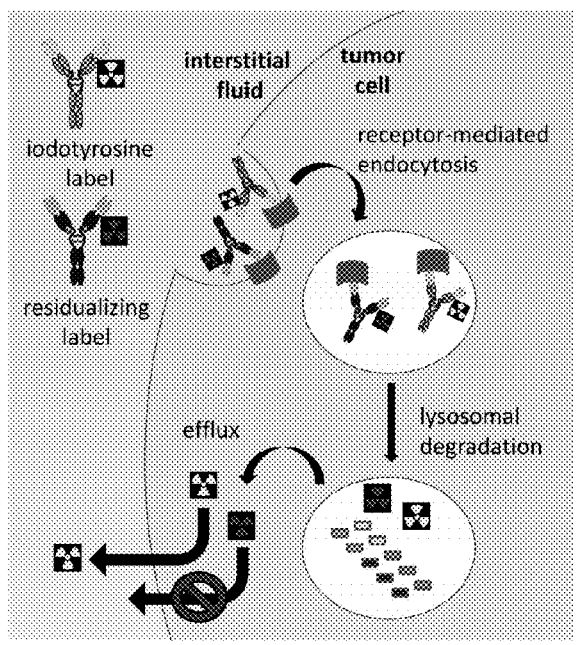

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described.

Unless defined otherwise, technical and scientific terms used herein have the same meaning as commonly understood by one of ordinary skill in the art to which this invention belongs, and are consistent with: Singleton et al, (1994) "Dictionary of Microbiology and Molecular Biology", 2nd Ed., J. Wiley & Sons, New York, N.Y.; and Janeway, et al (2001) "Immunobiology", 5th Ed., Garland Publishing, New York. When trade names are used herein, applicants intend to independently include the trade name product formulation, the generic drug, and the active pharmaceutical ingredient(s) of the trade name product

DEFINITIONS

Unless stated otherwise, the following terms and phrases as used herein are intended to have the following meanings:

"Radiohalogen" is any isotopic form of a halogen atom, including fluorine, chlorine, bromine, iodine, and astatine.

A "protein" is an organic compound made of amino acids arranged in a linear chain and joined together by peptide bonds between the carboxyl and amino groups of adjacent amino acid residues. Proteins are biological macromolecules and include enzymes, antibodies, interferon, lymphokines, cytokines, peptides, hormones, and growth factors. Many proteins are vital to metabolism, cell signaling, immune responses, cell adhesion, cell cycle effects, or have structural or mechanical functions, such as in muscle and the cytoskeleton. Functional classes of exemplary proteins include an antibody, a non-antibody alternative binding protein (Binz et al (2005) *Nature Biotechnology* 23(10):1257-1268; Skerra, A. (2007) *Current Opin. in Biotech.* 18:295-304), an interferon, a lymphokine, a cytokine, a peptide, a hormone, or a growth factor.

Proteins include those which have been modified with groups such as polyethyleneoxy groups (PEG) to impart optimized properties or derivatized with functional groups to facilitate conjugation with the radiohalogen-labeling reagents of the invention. For example, reactive amines such as lysine residues, may be derivatized with bifunctional linker reagents, such as SPDP (N-Succinimidyl 3-(2-pyridyldithio)-propionate) and LC-SPDP (Succinimidyl 6-(3-[2-pyridyldithio]-propionamido)hexanoate), commercially available from Thermo Fisher Scientific, Pierce Protein Biology Products, to give a reactive thiol group after reductive cleavage of the pyridyl disulfide group.

"Antibody" is used in the broadest sense and specifically covers monoclonal antibodies, polyclonal antibodies, multispecific antibodies (e.g., bispecific antibodies), dual-acting Fabs, and other antibody fragments. Antibodies may be murine, human, humanized, chimeric, or derived from other species. An antibody is a protein generated by the immune system that is capable of recognizing and binding to a specific antigen (Janeway, et al (2001) "Immunobiology", 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. Antibody also refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. Tumor-associated cell surface antigen polypeptides, i.e. tumor associated antigens (TAA), allows specific targeting of cancer cells for destruction via antibody-based therapies. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

Therapeutic monoclonal antibodies useful for the methods of the invention include trastuzumab (HERCEPTIN®, Genentech, Inc., Carter et al (1992) *Proc. Natl. Acad. Sci. USA,* 89:4285-4289; U.S. Pat. No. 5,725,856); anti-CD20 antibodies such as chimeric anti-CD20 "C2B8" (U.S. Pat. No. 5,736,137); rituximab (RITUXAN®), ocrelizumab, a chimeric or humanized variant of the 2H7 antibody (U.S. Pat. No. 5,721,108; WO 04/056312) or tositumomab (BEXXAR®); anti-IL-8 (St John et al (1993) *Chest,* 103: 932, and WO 95/23865); anti-VEGF antibodies including humanized and/or affinity matured anti-VEGF antibodies such as the humanized anti-VEGF antibody huA4.6.1 bevacizumab (AVASTIN®, Genentech, Inc., Kim et al (1992) *Growth Factors* 7:53-64, WO 96/30046, WO 98/45331); anti-PSCA antibodies (WO 01/40309); anti-CD40 antibodies, including S2C6 and humanized variants thereof (WO 00/75348); anti-CD11a (U.S. Pat. No. 5,622,700; WO 98/23761; Steppe et al (1991) *Transplant Intl.* 4:3-7; Hourmant et al (1994) *Transplantation* 58:377-380); anti-IgE (Presta et al (1993) *J. Immunol.* 151:2623-2632; WO 95/19181); anti-CD18 (U.S. Pat. No. 5,622,700; WO 97/26912); anti-IgE, including E25, E26 and E27 (U.S. Pat. No. 5,714,338; U.S. Pat. No. 5,091,313; WO 93/04173; U.S. Pat. No. 5,714,338); anti-Apo-2 receptor antibody (WO 98/51793); anti-TNF-alpha antibodies including cA2 (REMICADE®), CDP571 and MAK-195 (U.S. Pat. No. 5,672, 347; Lorenz et al (1996) *J. Immunol.* 156(4):1646-1653; Dhainaut et al (1995) *Crit. Care Med.* 23(9):1461-1469); anti-Tissue Factor (TF) (EP 0 420 937 B1); anti-human alpha 4 beta 7 integrin (WO 98/06248); anti-EGFR, chimerized or humanized 225 antibody (WO 96/40210); anti-CD3 antibodies such as OKT3 (U.S. Pat. No. 4,515,893); anti-CD25 or anti-tac antibodies such as CHI-621 SIMULECT® and ZENAPAX® (U.S. Pat. No. 5,693,762); anti-CD4 antibodies such as the cM-7412 antibody (Choy et al (1996) *Arthritis Rheum* 39(1):52-56); anti-CD52 antibodies such as CAMPATH-1H (Riechmann et al (1988) *Nature* 332:323-337); anti-Fc receptor antibodies such as the M22 antibody directed against Fc gamma RI as in Graziano et al (1995) *J. Immunol.* 155(10):4996-5002; anti-carcinoembryonic antigen (CEA) antibodies such as hMN-14 (Sharkey et al (1995) *Cancer Res.* 55(23Suppl): 5935s-5945s; antibodies directed against breast epithelial cells including huBrE-3, hu-Mc 3 and CHL6 (Ceriani et al (1995) *Cancer Res.* 55(23):5852s-5856s; and Richman et al (1995) *Cancer Res.* 55(23 Supp): 5916s-5920s); antibodies that bind to colon carcinoma cells such as C242 (Litton et al (1996) *Eur J. Immunol.* 26(1):1-9); anti-CD38 antibodies, e.g. AT 13/5 (Ellis et al (1995) *J.*

*Immunol.* 155(2):925-937); anti-CD33 antibodies such as Hu M195 (Jurcic et al (1995) *Cancer Res* 55(23 Suppl): 5908s-5910s and CMA-676 or CDP771; anti-CD22 antibodies such as LL2 or LymphoCide (Juweid et al (1995) *Cancer Res* 55(23 Suppl):5899s-5907s); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibody Ova-Rex; anti-idiotypic GD3 epitope antibody BEC2; anti-alpha v beta3 antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID 10 and the anti-HLA DR antibody Oncolym (Lym-1).

"Antibody fragments" comprise a portion of a full length antibody, generally the antigen binding or variable region thereof. Examples of antibody fragments include Fab, Fab', F(ab')$_2$, and Fv fragments; diabodies; linear antibodies; fragments produced by a Fab expression library, anti-idiotypic (anti-Id) antibodies, CDR (complementary determining region), ECD (extracellular domain), and epitope-binding fragments of any of the above which immunospecifically bind to cancer cell antigens, viral antigens or microbial antigens, single-chain antibody molecules; and multispecific antibodies formed from antibody fragments.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

"Monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see, U.S. Pat. No. 4,816,567). The "monoclonal antibodies" may also be isolated from phage antibody libraries using the techniques described in Clackson et al (1991) *Nature,* 352:624-628; Marks et al (1991) *J. Mol. Biol.,* 222:581-597; for example.

"Cysteine-engineered antibodies" are antibodies engineered from wild-type or parent antibodies by the introduction of one or more free cysteine amino acids. A "free cysteine amino acid" is a cysteine amino acid residue which has been engineered into a parent antibody, has a thiol functional group (—SH), and is not paired as, or otherwise part of, an intramolecular or intermolecular disulfide bridge. The free cysteine amino acid may be in the heavy chain, light chain or Fc region of an antibody. An engineered cysteine residue ("free cysteine thiol") is reactive with thiol-reactive labeling reagents. Cysteine-engineered antibodies include FAB antibody fragments (thioFab) and expressed, full-length, IgG monoclonal (ThioMab) antibodies (Junutula J. R., et al (2008) *Nat Biotechnol* 26:925-32; Shen et al (2012) *Nature Biotech.* 30(2):184-189; Junutula J. R. (2008) *J. Imm. Methods* 332(1,2):41-52; US 2011/0301334; U.S. Pat. No. 7,521,541; U.S. Pat. No. 7,855,275; U.S. Pat. No. 8,309,300, the contents of which are incorporated by reference). ThioFab and ThioMab antibodies have been conjugated through linkers at the newly introduced cysteine thiols with thiol-reactive linker reagents and drug-linker reagents to prepare antibody-drug conjugates (Junutula, J. R., et al (2010) *Clin. Cancer Res.* 16(19):4769-4778; U.S. Pat. No. 7,723,485).

"PEG" refers to a fragment of poly(ethylene glycol), a polymer of ethylene oxide, and includes 2 or more ethyleneoxy units (—$CH_2CH_2O$—).

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Synthesis of Iodine-Labeling Reagents

Iodine-labeling reagents may comprise three functional components: an iodotyrosine-like moiety, an activated group for antibody conjugation, and a residualizing anchor. The success of residualizing peptides, which contain iodotyrosine, suggested that a hydroxyphenyl residue is a sufficient scaffold on which to introduce radioiodine (Li, W. P., et al (2002) Bioconjug Chem., 13:721). This avoided the necessity of hazardous and expensive tin reagents and intermediates, which are necessary to produce other m-iodobenzoate derivatives (Vaidyanathan, G, et al (2001) Bioconjug Chem., 12:428; Shankar, S., et al (2003) Bioconjug Chem., 14:331; Vaidyanathan, G, et al (2012) Bioorg Med Chem, 20:6929-6939). The choice of the macrocyclic polyaminopolycarboxylic acid DOTA was based on both its known ability to residualize and on its accessibility, ease of derivatization, with a wide array of functional groups.

To avoid the necessity of numerous orthogonal protecting groups, a chemical reaction with the ability to combine multiple chemical components in a rapid, high yielding reaction and with ample flexibility in reactant structure was developed. These requirements are met by the Ugi multicomponent reaction involving a ketone or aldehyde, an amine, an isocyanide and a carboxylic acid to form a bis-amide (Ugi, I., et al (1959) Angewandte Chemie, 71:386; Domling, A.; Ugi, I. (2000) Angew Chem Int Ed Engl., 39:3168; Tei, L., et al (2009) Org Biomol Chem., 7:4406). The invention includes a facile, tin-free, three-step synthetic route to a residualizing probe amenable to oxidative radioiodination and antibody labeling. In particular, the multicomponent Ugi reaction is a surprising and efficient means for covalently linking three desired components of an iodine-labeling reagent: a charged residualizing anchor, a phenol for iodine incorporation, and an activated linker for protein conjugation.

Figure 2:
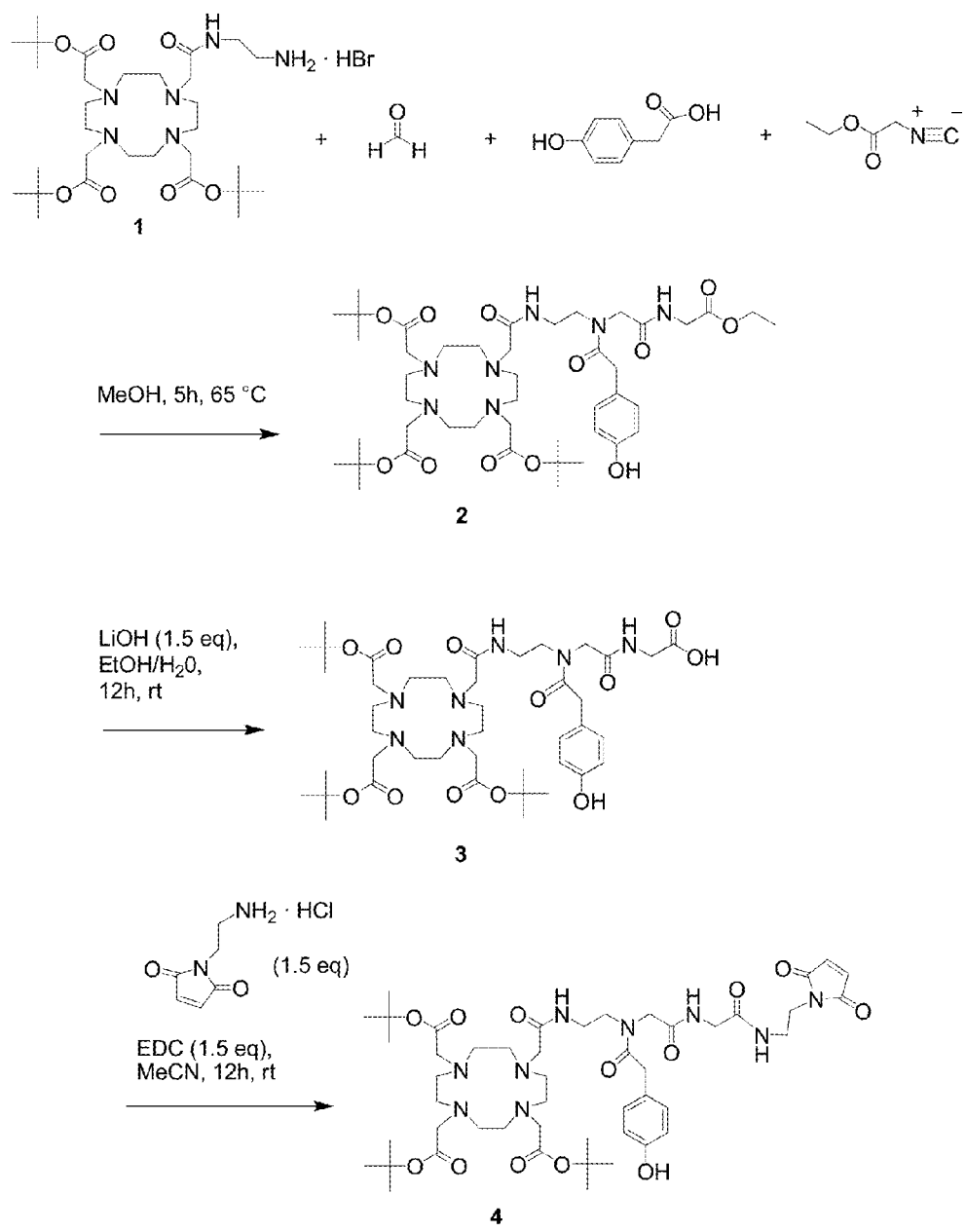
FIG. 2 shows a synthetic route to tri-tert-butyl 2,2',2"-(10-(14-(2,5-dioxo-2,5-dihydro-1H-pyrrol-1-yl)-6-(2-(4-hydroxyphenyl)acetyl)-2,8,11-trioxo-3,6,9,12-tetraazatetradecyl)-1,4,7,10-tetraazacyclododecane-1,4,7-triyl)triacetate 4.

Four commercially available Ugi components, formaldehyde, a primary amine-functionalized DOTA derivative 1, 4-hydroxyphenylacetic acid, and ethyl isocyanoacetate were reacted to form ethyl ester 2 (FIG. 2). The ethyl ester 2 was converted to the acid 3 by saponification using lithium hydroxide. Attempts to synthesize the succinimidyl ester (NHS) of this acid were unsuccessful, with the formation of dimers (phenolic esters) evident by mass spectrometry. Activated esters such as NHS are reactive with lysine residues of proteins. This problem was solved by changing from a lysine- to a cysteine-based conjugation strategy, taking advantage of recent developments in the use of antibody engineering to introduce site-specific cysteines (Junutula J R, et al (2008) Nat Biotechnol 26:925-32; Auf Dem Brinke, D., et al (1979) Biochem J, 180:273; U.S. Pat. No. 7,521,541). Such cysteine-engineered antibodies (Thio-Mabs) are useful for site-specific labeling through the highly-reactive cysteine thiol with reporter groups such as fluorescent dyes and radioisotopes (US 2010/0111856; US 2010/0221176). Certain ThioMab mutants are highly reactive with the maleimide group of a labeling reagent, forming a covalent linkage. Other thiol reactive electrophilic groups (E) include, but are not limited to, bromide, bromoacetamido, p-toluenesulfonate, iodide, pyridyl disulfide, isocyanato, isothiocyanato, and phosphoramidite.

FIG. 2 shows an exemplary synthetic route to tri-tert-butyl 2,2',2"-(10-(14-(2,5-dioxo-2,5-dihydro-1H-pyrrol-1-yl)-6-(2-(4-hydroxyphenyl)acetyl)-2,8,11-trioxo-3,6,9,12-tetraazatetradecyl)-1,4,7,10-tetraazacyclododecane-1,4,7-triyl)triacetate 4 from tri-tert-butyl 2,2',2"-(10-(2-((2-aminoethyl)amino)-2-oxoethyl)-1,4,7,10-tetraazacyclododecane-1,4,7-triyl)triacetate 1 (Examples 1-3). The maleimide group has been demonstrated to be compatible with the oxidative conditions of radioiodination (Khawli, L. A., et al (1992) Int J Rad Appl Instrum B., 19:289) which guided the synthetic route to introduce a maleimide group by coupling the acid 3 to N-(2-aminoethyl) maleimide using EDC, yielding the exemplary shelf-stable compound 4 (Example 3). Other reactive functionalities besides maleimide may be used in a radiohalogen-labeling reagent for labeling proteins, including thiol, amino, bromide, bromoacetamido, p-toluenesulfonate, iodide, hydroxyl, carboxyl, aldehyde, pyridyl disulfide, N-hydroxysuccinimide (NHS), azido, isocyanato, isothiocyanato, and phosphoramidite.

Figure 3:
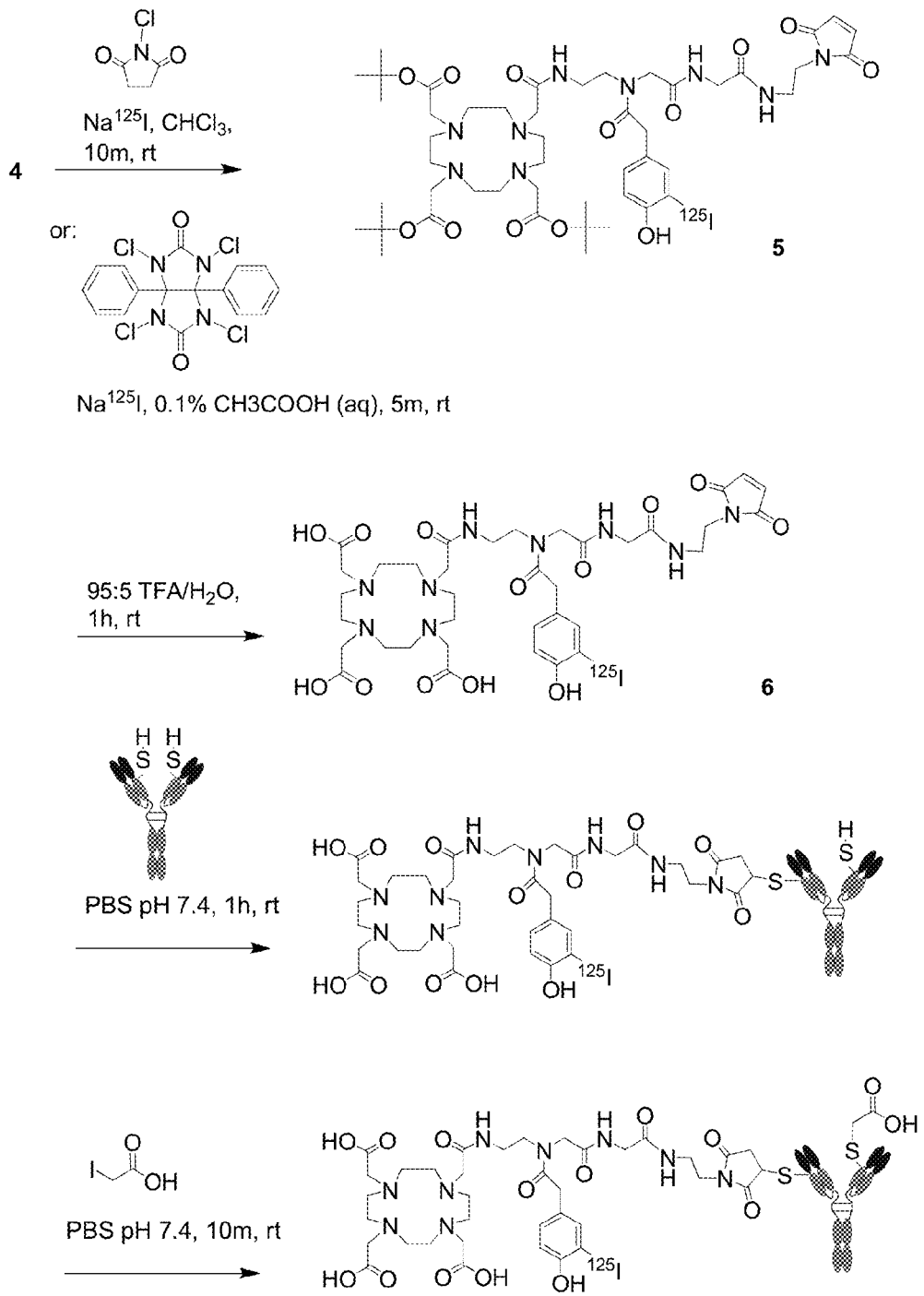
FIG. 3 shows a synthetic route to 6 and conjugation to a cysteine engineered antibody, followed by capping of unreacted cysteine thiols.

The radiochemical strategy shown on FIG. 3 uses the mild, water soluble oxidant, N-chlorosuccinimide, to achieve iodination on the hydroxyphenyl group of 4. Alternatively, maleimide 4 is sufficiently water soluble to allow a more efficient labeling in aqueous 0.1% acetic acid in a test tube pre-coated with the water-insoluble oxidizing agent, 1,3,4,6-tetrachloro-3α,6α-diphenylglucoluril (Iodogen, Thermo Scientific Pierce, Rockford, Ill., Cat. #28600; Fraker, P. J. and Speck, J. C., Jr. (1978) Biochem. Biophys. Res. Comm. 80(4):849-857). Intermediate [$^{125}$I]5 had a retention time of 15.5 minutes on reversed-phase HPLC and could be detected in terms of both [$^{127}$I] and [$^{125}$I] by mass spectrometry. Even though much greater radiochemical yield was possible by increasing the ratio of 4 to Na$^{125}$I, the highest possible specific activity of the radiolabeled intermediate 5 and higher conjugation yields was facilitated by avoiding saturation of available reduced thiols. The intermediate 5 was easily purified from free iodide and oxidant using reverse-phase solid-phase extraction cartridges. Acid deprotection yielded the triacid 6, with completeness of reaction monitored by reverse-phase radio-HPLC (FIG. 3). This 4-hydroxy-3-iodophenyl derivative of DOTA, 6, was designated [$^{125}$I] HIP-DOTA. After exhaustive removal of acid by repeated evaporation of toluene, the thiol-containing antibody could be introduced for thiol-maleimide coupling. Remaining free thiols in the radioimmunoconjugate were capped with iodoacetic acid to avoid dimerization or formation of adducts with thiol containing plasma or endogenous proteins. All radioimmunoconjugates were analyzed for purity by size-exclusion HPLC and compared to the profile of unlabeled antibodies, such as trastuzumab.

A radiohalogen-labeling reagent of the invention has the structure:

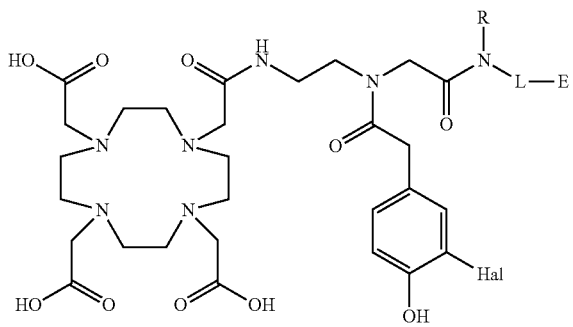

wherein

Hal is a radiohalide isotope selected from $^{123}$I, $^{124}$I, $^{125}$I, $^{131}$I, and $^{211}$At;

L is a linker selected from —($C_1$-$C_{12}$ alkylene)-C(O)NR—($C_1$-$C_{12}$ alkylene)-, —($C_1$-$C_{12}$ alkylene)-C(O)NR—($C_1$-$C_{12}$ alkylene)O—, —($C_1$-$C_{12}$ alkylene)-C(O)NR—($C_1$-$C_{12}$ alkylene)-C(O)$CH_2$—, —($C_1$-$C_{12}$ alkylene)-C(O)N(R)—, —($C_1$-$C_{12}$ alkylene)-C(O)NR—($C_2$-$C_8$ alkenylene)-, —($C_1$-$C_{12}$ alkylene)-C(O)NR—($C_2$-$C_8$ alkynylene)-, —($C_1$-$C_{12}$ alkylene)-C(O)NR($CH_2CH_2O$)$_n$—, —($C_1$-$C_{12}$ alkylene)-C(O)—, —($C_1$-$C_{12}$ alkylene)-C(O)NR($CH_2CH_2O$)$_1$$CH_2$C(O)—, and —($C_1$-$C_{12}$ alkylene)-C(O)NR($CH_2CH_2O$)$_n$$CH_2$—, where n is 1 to 6, R is H, $C_1$-$C_{12}$ alkyl, or $C_6$-$C_{20}$ aryl, and alkylene, alkenylene, alkynylene, alkyl, and aryl are optionally substituted with one or more groups selected from F, Cl, Br, I, —$CH_3$, —$CH_2CH_3$, —CH($CH_3$)$_2$, —$CH_2$CH($CH_3$)$_2$, —$CH_2NH_2$, —$CH_2CH_2NH_2$, —$CH_2$CHCH$_2NH_2$, —$CH_2$CH($CH_3$)$NH_2$, —$CH_2$OH, —$CH_2OCH_3$, —$CH_2CH_2$OH, —$CH_2CH_2OCH_3$, —C($CH_3$)$_2$OH, —CH(OH)CH($CH_3$)$_2$, —C($CH_3$)$_2CH_2$OH, —$CH_2CH_2SO_2CH_3$, —CN, —$CF_3$, —$CO_2$H, —$COCH_3$, —$CO_2CH_3$, —$CO_2$C($CH_3$)$_3$, —COCH(OH)$CH_3$, —$CONH_2$, —$CONHCH_3$, —CON($CH_3$)$_2$, —C($CH_3$)$_2$$CONH_2$, —$NO_2$, —$NH_2$, —$NHCH_3$, —N($CH_3$)$_2$, —$NHCOCH_3$, —N($CH_3$)$COCH_3$, —$NHS(O)_2CH_3$, —N($CH_3$)C($CH_3$)$_2$$CONH_2$, —N($CH_3$)$CH_2CH_2S(O)_2CH_3$, =O, —OH, —$OCH_3$, —OP(O)$_3$, —S(O)$_2$N($CH_3$)$_2$, —S(O)$_3$, —$SCH_3$, and —S(O)$_2CH_3$; and E is a reactive functional group selected from maleimide, thiol, amino, bromide, bromoacetamido, p-toluenesulfonate, iodide, hydroxyl, carboxyl, aldehyde, pyridyl disulfide, N-hydroxysuccinimide, azido, isocyanato, isothiocyanato, and phosphoramidite.

Exemplary radiohalogen-labeling reagents include:

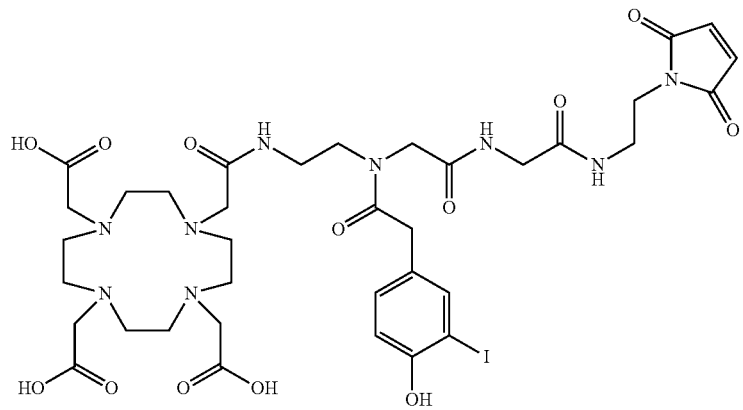

and

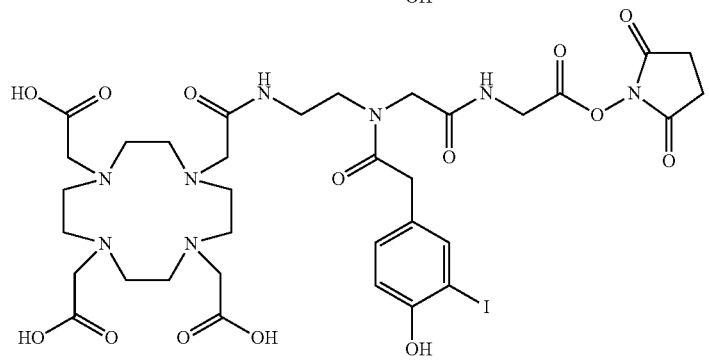

where I is an iodine isotope selected from $^{123}$I, $^{124}$I, $^{125}$I, and $^{131}$I.

Various functional groups of radiohalogen-labeling reagents, and intermediates or precursors, may be protected, such as the carboxylic acid and the phenolic hydroxyl groups. The carboxylic acid groups of the DOTA moiety may be protected as esters, such as tert-butyl esters. The phenolic hydroxyl group may be protected with a protecting group such as tert-butyl.

Synthesis of Iodine-Labeled Proteins

Peptide labeling methods are well known. See Haugland, 2003, *Molecular Probes Handbook of Fluorescent Probes and Research Chemicals*, Molecular Probes, Inc.; Brinkley, 1992, Bioconjugate Chem. 3:2; Garman, (1997) *Non-Radioactive Labeling: A Practical Approach*, Academic Press, London; Means (1990) *Bioconjugate Chem.* 1:2; Glazer et al (1975) *Chemical Modification of Proteins. Laboratory Tech-* niques in Biochemistry and Molecular Biology (T. S. Work and E. Work, Eds.) American Elsevier Publishing Co., New York; Lundblad, R. L. and Noyes, C. M. (1984) *Chemical Reagents for Protein Modification,* Vols. I and II, CRC Press, New York; Pfleiderer, G. (1985) "Chemical Modification of Proteins", *Modern Methods in Protein Chemistry,* H. Tschesche, Ed., Walter DeGryter, Berlin and New York; and Wong (1991) *Chemistry of Protein Conjugation and Cross-linking,* CRC Press, Boca Raton, Fla.); De Leon-Rodriguez et al (2004) Chem. Eur. J. 10:1149-1155; Lewis et al (2001) *Bioconjugate Chem.* 12:320-324; Li et al (2002) *Bioconjugate Chem.* 13:110-115; Mier et al (2005) *Bioconjugate Chem.* 16:240-237.

The proteins of the invention include cysteine engineered antibodies where one or more amino acids of any form of wild-type or parent antibody is replaced with a cysteine amino acid. The engineered cysteine amino acid is a free cysteine acid and not part of an intrachain or interchain disulfide unit. Any form of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. The cysteine engineered antibodies of the invention include monoclonal antibodies, humanized or chimeric monoclonal antibodies, antigen-binding fragments of antibodies, fusion polypeptides and analogs that preferentially bind cell-associated polypeptides. Cysteine engineered antibodies retain the antigen binding capability of their wild type, parent antibody counterparts.

FIG. 3 shows an exemplary synthetic route to 6 and conjugation to a cysteine engineered antibody, followed by capping of unreacted cysteine thiols.

A radiohalogen-labeled protein of the invention has the structure:

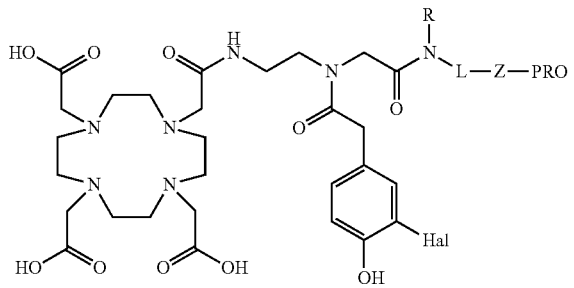

wherein

Hal is a radiohalide isotope selected from $^{123}$I, $^{124}$I, $^{125}$I, $^{131}$I, and $^{211}$At;

L is a linker selected from —($C_1$-$C_{12}$ alkylene)-C(O)NR—($C_1$-$C_{12}$ alkylene)-, —($C_1$-$C_{12}$ alkylene)-C(O)NR—($C_1$-$C_{12}$ alkylene)O—, —($C_1$-$C_{12}$ alkylene)-C(O)NR—($C_1$-$C_{12}$ alkylene)-C(O)$CH_2$—, —($C_1$-$C_{12}$ alkylene)-C(O)N(R)—, —($C_1$-$C_{12}$ alkylene)-C(O)NR—($C_2$-$C_8$ alkenylene)-, —($C_1$-$C_{12}$ alkylene)-C(O)NR—($C_2$-$C_8$ alkynylene)-, —($C_1$-$C_{12}$ alkylene)-C(O)NR($CH_2CH_2O$)$_n$—, —($C_1$-$C_{12}$ alkylene)-C(O)—, —($C_1$-$C_{12}$ alkylene)-C(O)NR($CH_2CH_2O$)$_n$$CH_2$C(O)—, and —($C_1$-$C_{12}$ alkylene)-C(O)NR($CH_2CH_2O$)$_n$$CH_2$—, where n is 1 to 6, R is H, $C_1$-$C_{12}$ alkyl, or $C_6$-$C_{20}$ aryl, and alkylene, alkenylene, alkynylene, alkyl, and aryl are optionally substituted with one or more groups selected from F, Cl, Br, I, —$CH_3$, —$CH_2CH_3$, —$CH(CH_3)_2$, —$CH_2CH(CH_3)_2$, —$CH_2NH_2$, —$CH_2CH_2NH_2$, —$CH_2CHCH_2NH_2$, —$CH_2CH(CH_3)NH_2$, —$CH_2OH$, —$CH_2OCH_3$, —$CH_2CH_2OH$, —$CH_2CH_2OCH_3$, —$C(CH_3)_2OH$, —CH(OH)CH($CH_3$)$_2$, —C($CH_3$)$_2$$CH_2$OH, —$CH_2CH_2SO_2CH_3$, —CN, —$CF_3$, —$CO_2$H, —$COCH_3$, —$CO_2CH_3$, —$CO_2$C($CH_3$)$_3$, —COCH(OH)$CH_3$, —$CONH_2$, —$CONHCH_3$, —CON($CH_3$)$_2$, —C($CH_3$)$_2$$CONH_2$, —$NO_2$, —$NH_2$, —$NHCH_3$, —N($CH_3$)$_2$, —$NHCOCH_3$, —N($CH_3$)$COCH_3$, —NHS(O)$_2$$CH_3$, —N($CH_3$)C($CH_3$)$_2$$CONH_2$, —N($CH_3$)$CH_2CH_2S(O)_2CH_3$, =O, —OH, —$OCH_3$, —OP(O)$_3$, —S(O)$_2$N($CH_3$)$_2$, —S(O)$_3$, —$SCH_3$, and —S(O)$_2$$CH_3$;

Z is selected from X, S, NH, $CH_2$C(O), C(O), ($CH_2CH_2O$)$_1$$CH_2$C(O), NHC(O), NHC(S), OP(O)$_2$, ($CH_2CH_2O$)$_1$$CH_2$X, and ($C_1$-$C_{12}$ alkylene)X, where X is

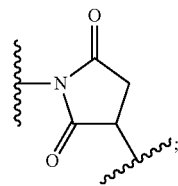 [SMILES: *C1CC(=O)N(*)C1=O]

and

PRO is a protein selected from an antibody, an interferon, a lymphokine, a cytokine, a peptide, a hormone, and a growth factor. Antibodies include those forms which are useful for imaging, including domain antibodies, minibodies, diabodies, and affibodies The maleimide derivative [$^{125}$I]HIP-DOTA 6 has the potential to be conjugated to any thiol-containing protein, including cysteine-engineered antibodies (Junutula, J. R., et al (2008) *Nat Biotechnol.,* 26:925-932; U.S. Pat. No. 7,521,541; U.S. Pat. No. 7,855,275; U.S. Pat. No. 8,309,300), interchain disulfides of traditional antibodies following reduction, and thio-derivatized proteins. The ability to conjugate a residualizing probe to thiols may be useful as a quantitative means to estimate cumulative drug delivery of antibody-drug conjugates in which chemotherapeutic drugs are conjugated using similar chemical methodologies (Wu, A. M., et al (2005) *Nat Biotechnol.,* 23:1137). In addition, a residualizing halogen probe could benefit the development of radioimmunotherapeutic agents labeled with the (beta) β-emitter, $^{131}$I, or alternatively with the (alpha) α-emitting radionuclide astatine-211 ($^{211}$At) (Table 1). See Brechbiel, M. W. (2007) *Dalton Trans.,* 4918). Moreover, aside from its residualizing properties, the presence of DOTA in [$^{125}$I]HIP-DOTA lends the possibility of incorporating a metal to yield a multi-modal probe. The DOTA chelate forms very kinetically stable complexes with larger +3 metal cations including the γ emitter $^{111}$In, the low energy beta/negatron (β$^-$) emitter lutetium-177 ($^{177}$Lu), the high energy β$^-$ emitter yttrium-90 ($^{90}$Y), the positron (β$^+$) emitter yttrium-86 ($^{86}$Y), and non-radioactive gadolinium ($^{nat}$Gd) as a magnetic resonance spectroscopy contrast agent (Boswell, C. A., et al (2007) *Nucl Med Biol,* 34:757).

Figure 9:
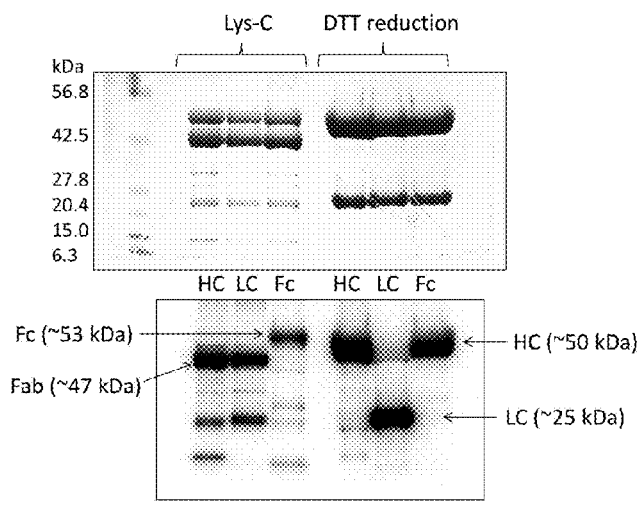
FIG. 9 shows SDS-PAGE analysis by protein staining (top) and phosphorimaging (bottom) of trastuzumab labeled site specifically with [$^{125}$I]6 through its heavy chain (HC-A114C), light chain (LC-V205C), and Fc (Fc-S396C) region. Digestion of antibodies with the endoprotease, Lys-C, results in cleavage between the Fab and Fc regions. In contrast, dithiothreitol (DTT) reduction separates the heavy (attached to Fc) and light chains.

The site-specificity of labeling was confirmed by SDS-PAGE analysis including both protein staining and phosphorimaging (FIG. 9). Digestion with the endoprotease Lys-C was able to distinguish radiolabeled Fc from Fab.

Similarly, reduction by dithiothreitol was able to resolve radiolabeled light chain (LC) from radiolabeled HC/Fc regions.

FIG. 9 shows SDS-PAGE analysis by protein staining (top) and phosphorimaging (bottom) of trastuzumab labeled site specifically with [$^{125}$I]6 through its heavy chain (HC-A114C), light chain (LC-V205C), and Fc (Fc-S396C) region. Digestion of antibodies with the endoprotease, Lys-C, results in cleavage between the Fab and Fc regions. In contrast, dithiothreitol (DTT) reduction separates the heavy (still attached to Fc) and light chains. Differential exposure of radioactivity in selected bands is evident despite equal loading of proteins, demonstrating the site-specificity of labeling.

Differences in stability between the heavy chain (HC-A114C), light chain (LC-V205C), and crystallizable fragment (Fc-S396C) radioimmunoconjugate variants of cysteine-engineered antibodies ("ThioMab") were anticipated (Shen et al (2012) Nat. Biotechnol. 30:184-189). Cysteine-engineered mutant positions are numbered according to the Kabat numbering scheme. Each of the [$^{125}$I]6-labeled trastuzumab derivatives was incubated in mouse plasma at 37° C. by an in vitro plasma stability assay. Consistent with the stabilities of antibody-drug conjugates reported in Shen et al, the rank order of plasma stability for the site-specific ThioMab conjugates was LC>HC>Fc.

Figure 10:
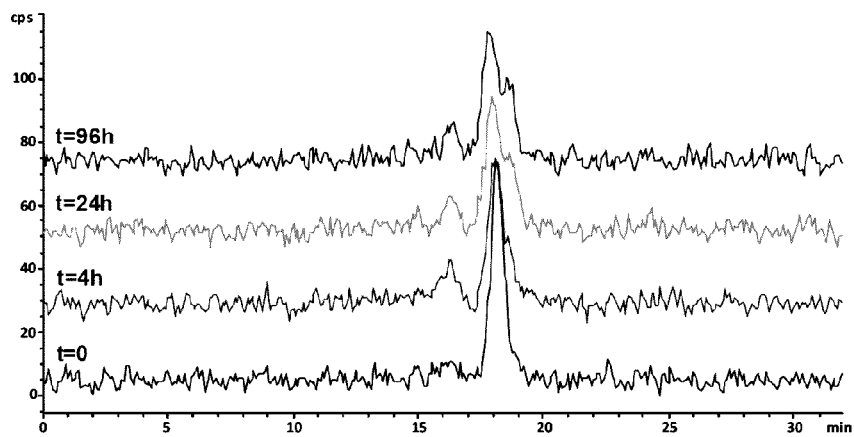
FIG. 10 shows an HPLC chromatogram with radioisotope detection (counts per second, cps) of [I-125]6-HC-A114C thio-trastuzumab stability in mouse plasma at 37° C.
Figure 11:
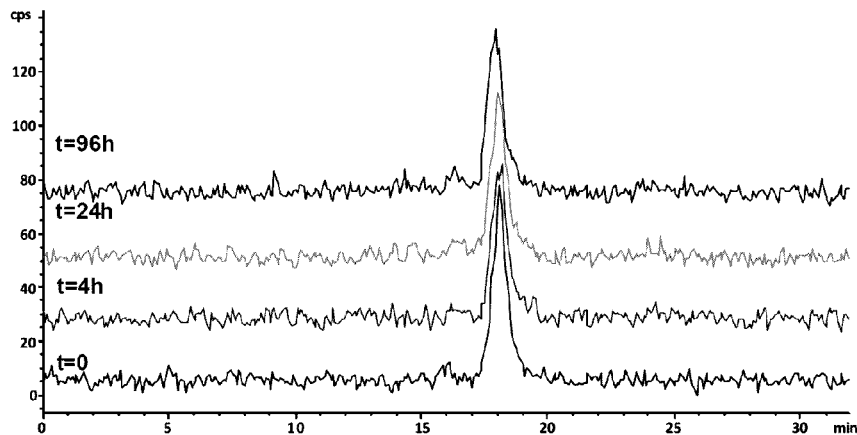
FIG. 11 shows an HPLC chromatogram with radioisotope detection (counts per second, cps) of [I-125]6-LC-V205C thio-trastuzumab stability in mouse plasma at 37° C.
Figure 12:
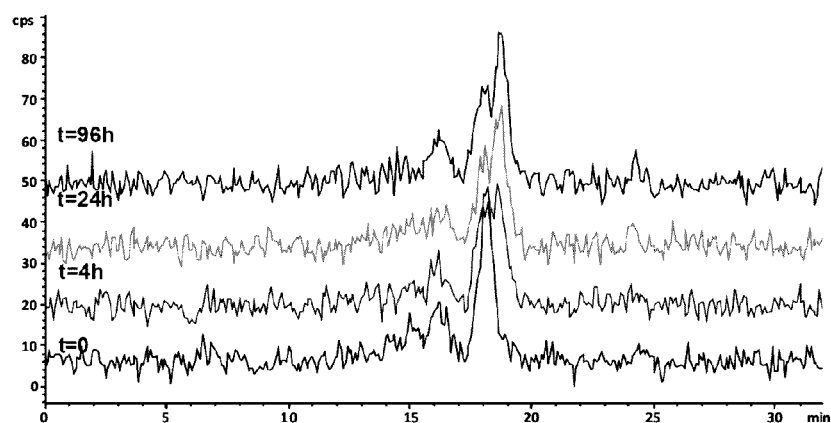
FIG. 12 shows an HPLC chromatogram with radioisotope detection (counts per second, cps) of [I-125]6-FC-S396C thio-trastuzumab stability in mouse plasma at 37° C.

FIG. 10 shows an HPLC chromatogram with radioisotope detection (counts per second, cps) of [I-125]6-HC-A114C thio-trastuzumab stability in mouse plasma at 37° C. FIG. 11 shows an HPLC chromatogram with radioisotope detection (counts per second, cps) of [I-125]6-LC-V205C thio-trastuzumab stability in mouse plasma at 37° C. FIG. 12 shows an HPLC chromatogram with radioisotope detection (counts per second, cps) of [I-125]6-FC-S396C thio-trastuzumab stability in mouse plasma at 37° C. These site specific differences in stability likely result from the local electrostatic environment (i.e. charged residues) causing variations in the rate of succinimide ring hydrolysis, which prevents further maleimide exchange with reactive thiols and enhances stability. The loss of the main (intact) peak at 18 min was accompanied by the appearance of two new peaks. An earlier peak at 16.5 min was attributed to protein aggregation and/or dimerization, while a later peak at 19 min was consistent with the retention time of albumin, an abundant plasma protein that is known to possess a reactive thiol.

Biodistribution of Radioiodine-Labeled Proteins

A biodistribution study was performed to evaluate the ability of HIP-DOTA to residualize in a previously validated xenograft mouse model of HER2-expressing breast cancer (Pastuskovas, C. V., et al (2012) *Mol Cancer Ther.*, 11:752). The iodoacetic acid-capped, HIP-DOTA $^{125}$I-6-trastuzumab was directly compared with traditional, tyrosine-labeled $^{125}$I-trastuzumab prepared by indirect Iodogen method (Chizzonite, R., et al (1991) *J Immunol.*, 147:1548). See Example 7. The same antibody labeled through lysine residues with $^{111}$In-DOTA, a known residualizing probe, was co-administered with each radioiodinated antibody to serve as an internal control. Simultaneous measurement of both $^{125}$I and $^{111}$In in a single sample is feasible due to the distinct gamma energies of these two radionuclides.

Figure 7A:
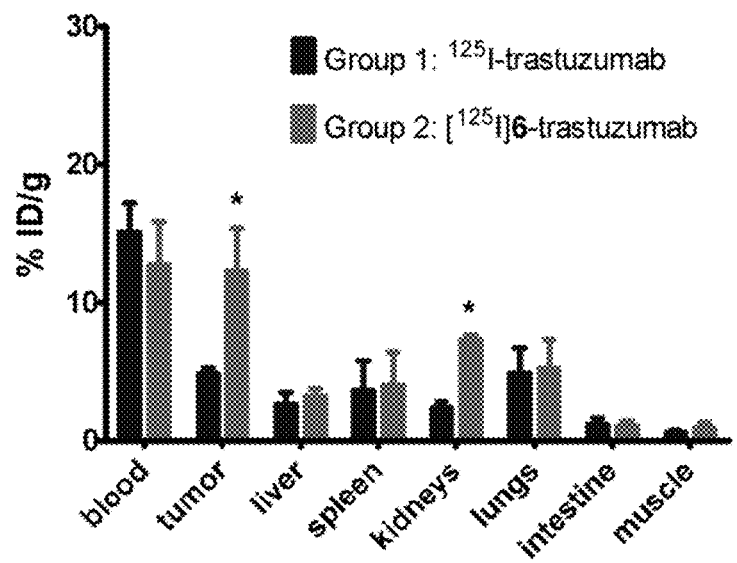
FIGS. 7A and 7B show biodistribution of radiolabeled trastuzumab in a HER2 expressing xenograft and various murine tissues. Mice were divided into two groups, with all mice receiving a mixture of $^{125}$I- and $^{111}$In-DOTA-labeled trastuzumab. Trastuzumab was labeled with $^{125}$I by traditional tyrosine modification for Group 1, while mice in Group 2 received $^{125}$I-6-trastuzumab ([$^{125}$I]HIP-DOTA-trastuzumab. Uptake is expressed as percentage of injected dose per gram of tissue (% ID/g). Statistically significant differences by unpaired t test are indicated by asterisk (*P, 0.05).
Figure 7B:
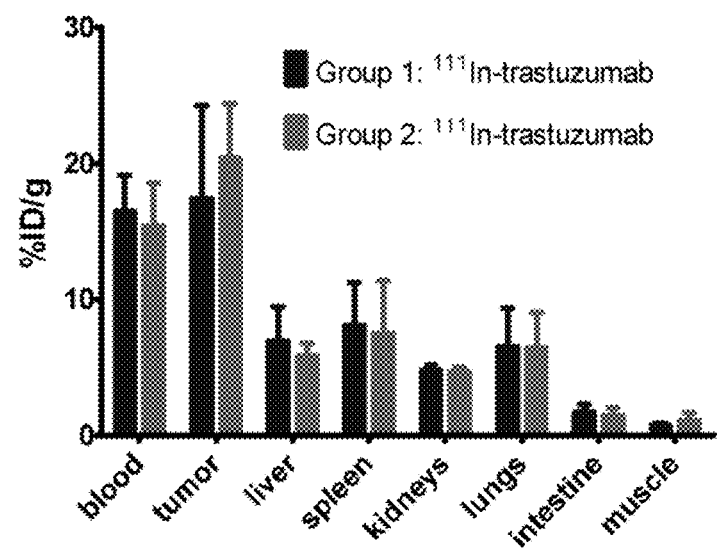

FIGS. 7A and 7B show biodistribution of radiolabeled trastuzumab in a HER2 expressing xenograft and various murine tissues. Mice were divided into two groups, with all mice receiving a mixture of $^{125}$I- and $^{111}$In-DOTA-labeled trastuzumab. Trastuzumab was labeled with $^{125}$I by traditional tyrosine modification for Group 1, while mice in Group 2 received $^{125}$I-6-trastuzumab ([$^{125}$I]HIP-DOTA-trastuzumab. Uptake is expressed as percentage of injected dose per gram of tissue (% ID/g). Statistically significant differences by unpaired t test are indicated by asterisk (*P, 0.05).

Tumor uptake of [$^{125}$I]HIP-DOTA-trastuzumab was more than double that of $^{125}$I-trastuzumab (12.2±3.1 versus 4.8±0.4 percentage of injected dose per gram) at 3 days post tracer injection (FIG. 7A). By comparison, 3-day tumor uptake of $^{111}$In-DOTA-trastuzumab was similar between both groups with an overall merged value of 19.1±5.4 percentage of injected dose per gram (FIG. 7B). These data suggest that [$^{125}$I]HIP-DOTA-cysteine, the expected radiocatabolite, is residualized to a greater extent than iodotyrosine. Aside from tumor, no other major differences in tissue uptake between the three labeling methods were observed, except for a higher renal uptake of radioactivity for [$^{125}$I]HIP-DOTA-trastuzumab relative to $^{125}$I-trastuzumab. Renal levels of radioactivity following injection of $^{125}$I-, $^{125}$I-6-, and $^{111}$In-DOTA-labeled trastuzumab were roughly 2, 7, and 5% ID/g respectively.

When conjugated to trastuzumab, a marketed anti-HER2 antibody (HERCEPTIN®, Genentech, Inc.), this novel probe demonstrated a 154% increase, relative to traditional tyrosine radioiodination, in tumor uptake at 3 days post-injection. Overall, the synthetic route to [$^{125}$I]HIP-DOTA, a novel residualizing radioiodine probe, is potentially useful for other targeted radioimmunotherapy of cancer, and may also benefit translational research efforts for antibodies across multiple therapeutic areas.

A 154% increase in tumor uptake was observed for [$^{125}$I]HIP-DOTA-trastuzumab relative to traditional tyrosine radioiodination at 3 days post-injection. However the level of tumor uptake still fell short of the radiometal $^{111}$In-DOTA. One plausible explanation is that the overall degree of charge and polarity of [$^{125}$I]HIP-DOTA-cysteine is inferior to that of $^{111}$In-DOTA-lysine. One might hypothesize that the presence of the metal in the latter may be the reason for this discrepancy; however, previous studies showed that the presence of In$^{3+}$ did not affect the level of residualization in antibodies labeled with DTPA-appended radioiodinated peptides (Govindan, S. V., et al (1999) *Bioconjug Chem.*, 10:231). DTPA has faster chelation kinetics so DOTA might not pick up metal in circulation as efficiently as DTPA, so the Govindan studies might only apply to DTPA since it is hard not to get a metal in the DTPA, not true for DOTA. Pre-chelation is a plausible strategy to improve the level of residualization. Furthermore, the possibility exists that chelates may scavenge iron or other adventitious metals in tissue culture media or perhaps even in vivo (Vaidyanathan, G, et al (2012) *Bioorg Med Chem*, 20:6929-6939). Another possibility is that dehalogenation, cleavage of the halogen-carbon bond, is affecting the probe's tumor retention.

Diffusion of radioiodotyrosine following lysosomal proteolysis is not the only hurdle to tumor accretion faced by internalizing antibodies that are radioiodinated through tyrosine residues. Dehalogenation is a second problem that contributes to the underlying discrepancy in tumor uptake between targeted molecules labeled with radiohalogens and radiometals. Dehalogenation is caused by class of enzymes termed dehalogenases which, although mostly concentrated in the thyroid, are also present elsewhere including the liver and kidneys (Gnidehou, S., et al (2004) *Faseb J*, 18:1574). The use of organostannane precursors to prepare charged meta-iodobenzoate derivatives as residualizing iodine probes is intended to avert this problem by eliminating the presence of a phenol group, thus escaping specific molecular recognition by iodotyrosine dehalogenases (Vaidyanathan, G., et al (2001) *Bioconjug Chem.*, 12:428; Shankar, S., et al (2003) *Bioconjug Chem.*, 14:331; Vaidyanathan, G., et al (2012) *Bioorg Med Chem*, 20:6929-6939). The use of similar strategies for non-residualizing iodine probes that are more resistant to enzymatic dehalogenation has been reported (Khawli, L. A., et al (1992) *Int J Rad Appl Instrum B.*, 19:289; Khawli, L. A., et al (1989) *Int J Rad Appl Instrum B.*, 16:727; Zalutsky, M. R., et al (1988) *Cancer Res*, 48:1446). 2-Iodophenol derivatives may be incorporated into residualizing probes (Govindan, S. V., et al (1999) *Bioconjug Chem.*, 10:231; Stein, R., (2005) *Clin Cancer Res*, 11:2727). Efflux of iodotyrosine following lysosomal proteolysis is problematic, along with enzymatic dehalogenation. Dehalogenases are specific for mono- or diiodinated L-tyrosine, therefore the D-tyrosine-containing IMP-R4 and the Ugi-derived [$^{125}$I]HIP-DOTA may not be recognized by these enzymes.

The higher renal uptake associated with [$^{125}$I]HIP-DOTA-trastuzumab, relative to $^{125}$I-trastuzumab, was expected based on reports of residualizing labels (Pastuskovas, C. V., et al (2012) *Mol Cancer Ther*, 11:752). In a surprising and unexpected result, the kidney uptake of radioactivity for the compound of the invention, [$^{125}$I]HIP-DOTA-trastuzumab, was higher than for $^{111}$In-DOTA-trastuzumab. Since the brush border of the renal proximal tubules has a polyanionic charge (Takahashi, S., et al (2004) *Kidney Int.*, 66:1556), it is expected that positively charged molecules would have a tendency to be retained in the kidneys (Boswell, C. A., et al (2010) *Bioconjug Chem.*, 21:2153). Indeed, administration of the basic amino acid lysine has been used to minimize unwanted renal retention of positively charged peptides (Hammond, P. J., et al (1993) *Br J Cancer.*, 67:1437). Even though [$^{125}$I]HIP-DOTA labeled protein catabolites of the residualizing moieties are expected to bear a net negative charge, it is plausible that protonation of one or more amines within the DOTA-like macrocycle at physiological pH may be producing enough positive charge to promote kidney uptake. In this case, complexation with a non-radioactive metal (e.g. $In^{3+}$, $Gd^{3+}$, or $Fe^{3+}$) may avoid the elevated renal uptake. Alternatively, the higher renal uptake of radioactivity following administration of [$^{125}$I]HIP-DOTA-trastuzumab relative to $^{111}$In-DOTA-trastuzumab may reflect a more efficient level of tumor residualization of radioactive catabolites for the latter.

Figure 13:
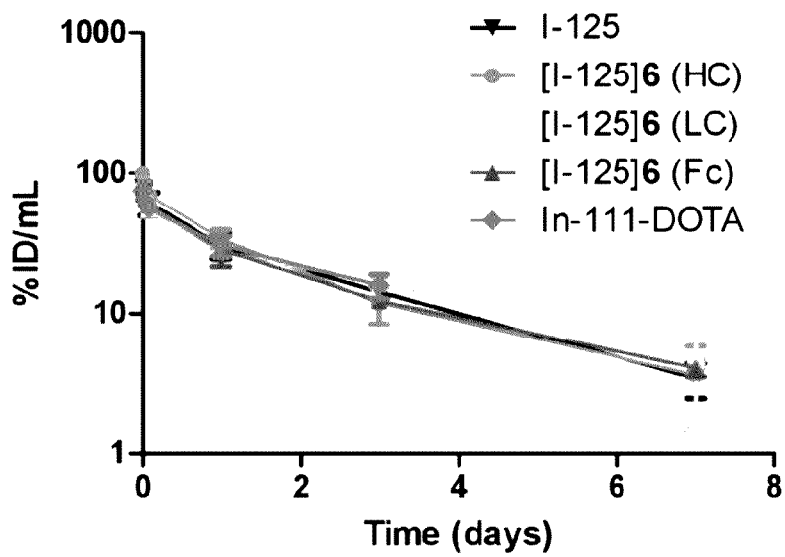
FIG. 13 shows plasma pharmacokinetics of trastuzumab was labeled with $^{125}$I by traditional tyrosine modification (black), by site-specific (HC-A114C/LC-V205C/Fc-S396C) modification in the heavy chain, light chain, and framework region with [$^{125}$I]6, or by lysine modification with $^{111}$In-DOTA. Uptake is expressed as percentage of injected dose per gram of tissue (% ID/g).

The plasma clearance profiles for all three radioimmunoconjugates: trastuzumab labeled site specifically with [$^{125}$I]6 through its heavy chain (HC-A114C), light chain (LC-V205C), and Fc (Fc-S396C) region, were overlapping (FIGS. 13, 14) indicating that the tumor uptakes of radioactivity for $^{111}$In-DOTA-, [$^{125}$I]6- and $^{125}$I-labeled trastuzumab were not influenced by systemic exposure and that modification of the antibody with [$^{125}$I]6 did not deleteriously affect its pharmacokinetics. The lack of difference among [$^{125}$I]6-trastuzumab variants, despite differences in plasma stability, reflects the inability of the radiometric pharmacokinetic assay to distinguish between intact antibody and [$^{125}$I]6-albumin, a likely product of maleimide exchange with reactive thiols (Shen et al (2012) *Nature Biotech.* 30(2):184-189).

Figure 14:
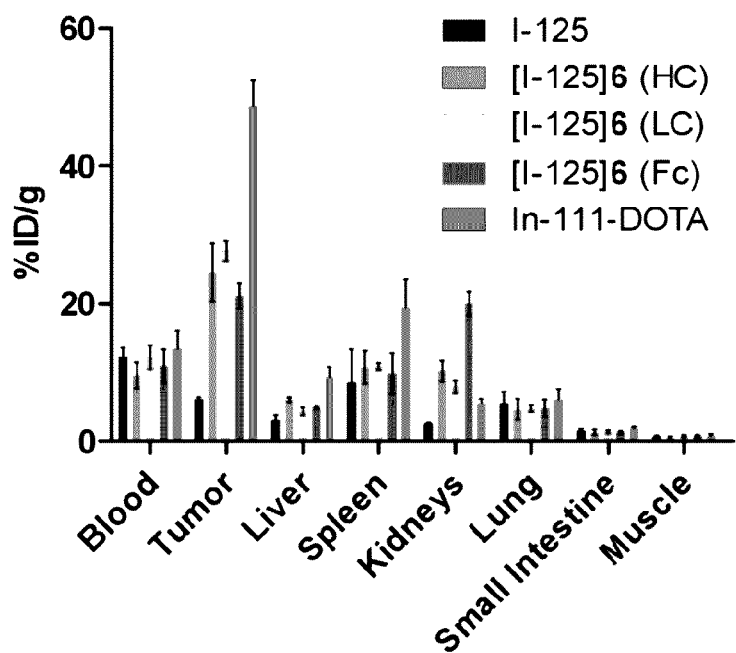
FIG. 14 shows biodistribution at 3 days of trastuzumab radiolabeled by site-specific (HC-A114C/LC-V205C/Fc-S396C) modification in the heavy chain, light chain, and framework region with [$^{125}$I]6, or by lysine modification with $^{111}$In-DOTA in KPL-4 xenograft-bearing mice.

At 3 days, tumor uptake for each of the three [$^{125}$I]6-trastuzumab variants was more than triple that of $^{125}$I-trastuzumab with values of 24.6±4.2 (HC-A114C), 27.7±1.4 (LC-V205C), 21.2±1.8 (Fc-S396C), and 6.1±0.3 (tyrosine-modified) percentage of injected dose per gram (% ID/g), respectively (FIG. 14). By comparison, 3-day tumor uptake of $^{111}$In-DOTA-trastuzumab was even higher at 48.7±3.8% ID/g. These data suggest that [$^{125}$I]6-associated catabolites are residualized to a greater extent than [$^{125}$I]iodotyrosine. Apart from tumor, the radioactivity levels in tissues obtained by trastuzumab labeled by the five different methods were largely similar. A higher renal uptake of radioactivity was observed for [$^{125}$I]6-trastuzumab, particularly the Fc variant, relative to [$^{125}$I]-trastuzumab. Renal levels of radioactivity following injection of [$^{125}$I], [$^{125}$I]6-(HC), [$^{125}$I]6-(LC), [$^{125}$I]6-(FC), and $^{111}$In-DOTA-labeled trastuzumab were roughly 3, 10, 8, 20 and 6% ID/g, respectively. In addition, both splenic and hepatic uptake of $^{111}$In were higher than for any of the [$^{125}$I]-labeled molecules.

At 1 week, the trends in tumor and tissue uptake were somewhat similar to those observed in the 3-day data, although the residualization of $^{111}$In-DOTA appears to be more sustained than [$^{125}$I]6 (FIG. 14). Mean tumor uptakes were 6.9±3.7 (HC-A114C), 8.2±3.8 (LC-V205C), 5.9±0.7 (Fc-S396C), 1.7±0.3 (tyrosine-modified), and 21.2±5.6 (111In-DOTA) % ID/g, respectively. The levels of $^{111}$In uptake in % ID/g for liver (7.2) and spleen (13) were considerably higher than for any of the $^{125}$I-labeled analogs.

Figure 15:
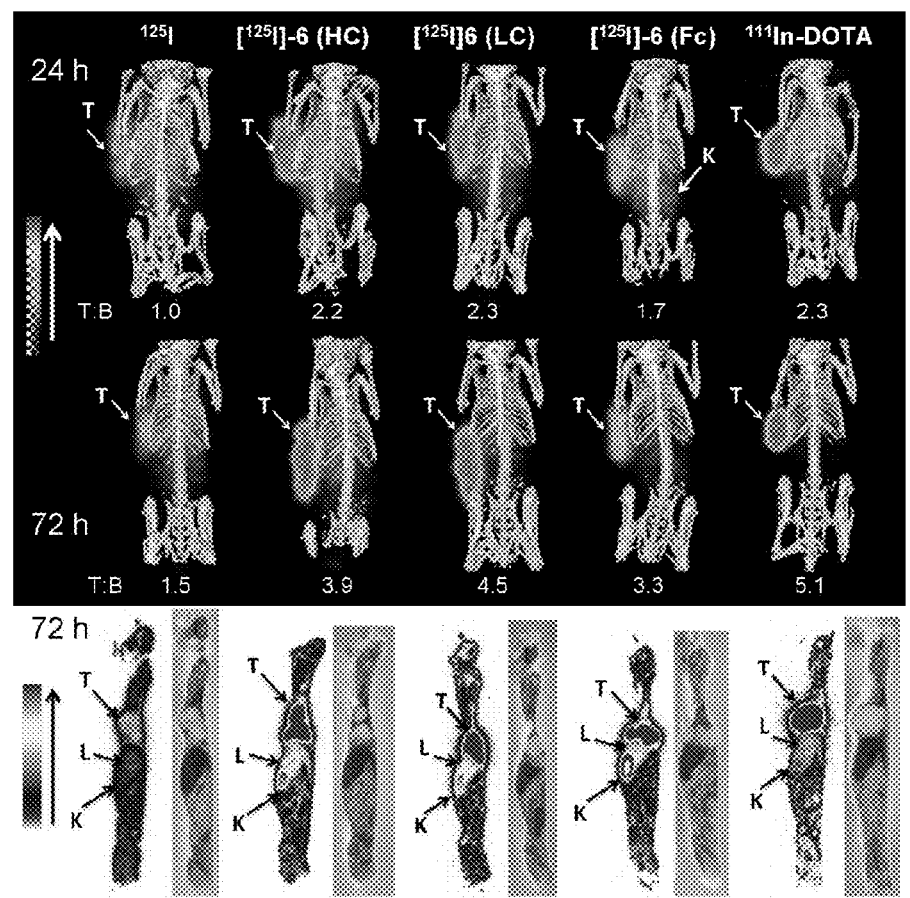
FIG. 15 shows SPECT-CT imaging (upper) at 24 and 72 hours and whole-body autoradiographic imaging (lower) at 72 hours indicate relative degrees of tracer residualization in KPL-4 xenograft-bearing mice following intravenous administration of trastuzumab radiolabeled by 5 different methods. In the three-dimensional volume renderings from a coronal perspective (upper), the skeletal images are derived from the X-ray (anatomical) CT data while the relative levels of radioactivity from the SPECT data are indicated in a false-color scale. Tumor-to-blood (T:B) ratios of radioactive uptake are shown. Post-mortem cryosection images from a sagittal perspective (lower) were acquired from the same mice as in the upper panel. False-colored phosphorimages (left) and digital photographs (right) are shown for each mouse in the tumoral plane. Tissues are labeled as tumor (T), liver (L) and kidney (K).

Non-invasive single photon emission computed tomography (SPECT) imaging was per-formed in live, anesthetized KPL-4 tumor-bearing mice in order to complement the biodistribution study arm (FIG. 15, upper). X-ray computed tomography (CT) was performed prior to SPECT without movement or bed adjustment to allow anatomical coregistration of radioactivity with tissue structures. Seventy-two-hour SPECT-CT images of mice receiving a single intravenous injection of radiolabeled trastuzumab qualitatively revealed tumor-to-background ratios in the following rank order: $^{111}$In-DOTA>$^{125}$I-6 (LC-V205C)>$^{125}$I-6 (HC-A114C)>$^{125}$I-6 (Fc-S396C)>$^{125}$I (tyrosine-modified). The better agreement between $^{111}$In-DOTA and [$^{125}$I]6 by SPECT-CT in FIG. 15, relative to FIGS. 13 and 14, may be explained by higher receptor occupancy and/or altered internalization rates due to the higher doses of radiolabeled antibody necessary for image acquisition.

Whole-body localization of radioactivity in KPL-4 tumor-bearing mice was determined by autoradiography (FIG. 15, lower). Digital photographs of the sagittal cryosections allow anatomical coregistration. The same rank order of relative tumor uptake (upper panel) was qualitatively observed: $^{111}$In-DOTA>[$^{125}$I]I6 (LC-V205C)>[$^{125}$I]6 (HC-A114C)>[$^{125}$I]6 (Fc-S396C)>$^{125}$I (tyrosine-modified). Elevated renal uptake, especially for the Fc variant of $^{125}$I-6-trastuzumab, was evident by both SPECT and autoradiography and recapitulated the data obtained by organ harvest in the plasma pharmacokinetic study of FIG. 13 and biodistribution of FIG. 14. In the midline plane (lower panel), a strikingly high uptake of radioactivity in the thyroid gland was the dominant feature in the $^{125}$I-trastuzumab (tyrosine-modified) autoradiograph (FIG. 15) despite the NaI blocking doses administered at both 24 and 1 h prior to dosing. The absence of this feature in the SPECT images could be explained by image artifacts near the top/bottom of the images or by the thyroid lying outside of the reconstructed field-of-view, which is smaller for SPECT than for CT on the system employed. In contrast, mostly blood pool uptake was visible in the midline plane for the other 4 variants (FIG. 15). The image quality and resolution for $^{111}$In-DOTA was noticeably inferior to the $^{125}$I-labeled variants, as evident from the degree of pixelation and bleed-over (FIG. 15). This observation may be attributed to the roughly ten-fold γ (gamma) energy of $^{111}$In relative to $^{125}$I.

Pharmacokinetics of Radioiodine-Labeled Proteins

Figure 8A:
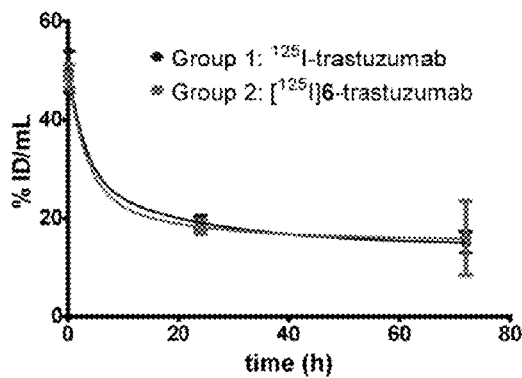
FIGS. 8A and 8B show blood pharmacokinetics of radiolabeled trastuzumab in a HER2 expressing xenograft and various murine tissues. Mice were divided into two groups, with all mice receiving a mixture of $^{125}$I- and $^{111}$In-DOTA-labeled trastuzumab. Concentrations are expressed as percentage of injected dose per milliliter of blood (% ID/mL). Trastuzumab was labeled with $^{125}$I by traditional tyrosine modification for Group 1, while mice in Group 2 received $^{125}$I-6-trastuzumab, where 6=HIP-DOTA.
Figure 8B:
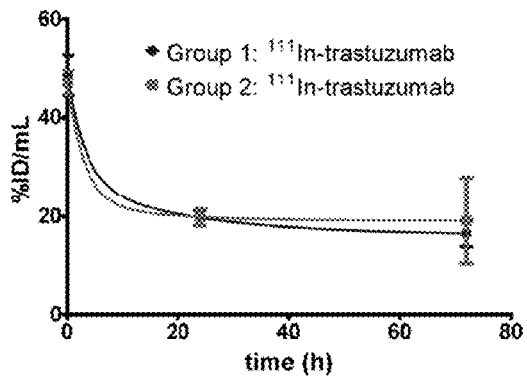

FIGS. 8A and 8B show blood pharmacokinetics of radiolabeled trastuzumab in a HER2 expressing xenograft and various murine tissues. Mice were divided into two groups, with all mice receiving a mixture of $^{125}$I- and $^{111}$In-DOTA-labeled trastuzumab. Concentrations are expressed as percentage of injected dose per milliliter of blood (% ID/mL). Trastuzumab was labeled with $^{125}$I by traditional tyrosine modification for Group 1, while mice in Group 2 received $^{125}$I-6-trastuzumab, where 6=HIP-DOTA.

A blood pharmacokinetics study was performed in parallel to the biodistribution study to ensure that the tumor uptake of radioactivity for [$^{125}$I]HIP-DOTA- and $^{125}$I-labeled trastuzumab was not influenced by systemic exposure (FIG. 8A). The pharmacokinetics profiles of the two radiolabeled antibodies were overlapping and similar to the respective curves for $^{111}$In-trastuzumab (FIG. 8B). These data suggest that, as expected, blood clearance is similar across all three labeling methods, indicating that modification of the antibody with [$^{125}$I]HIP-DOTA did not deleteriously affect its pharmacokinetics.

Imaging of Radiohalogen Labeled Proteins

Radiohalogen labeled proteins, including cysteine engineered antibodies, of the invention are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Chen et al (2004) *Bioconjugate Chem.* 15:41-49; (v) bioluminescence; (vi) fluorescence; and (vii) ultrasound. Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging helps minimize the number of animals needed for preclinical studies.

Pharmaceutical Compositions

Pharmaceutical compositions or formulations of the present invention include a labeled protein of the invention, and one or more pharmaceutically acceptable carrier, glidant, diluent, or excipient.

Pharmaceutical compositions encompass both the bulk composition and individual dosage units comprised of more than one (e.g., two) pharmaceutically active agents including a labeled protein along with any pharmaceutically inactive excipients, diluents, carriers, or glidants. The bulk composition and each individual dosage unit can contain fixed amounts of the aforesaid pharmaceutically active agents. The bulk composition is material that has not yet been formed into individual dosage units. An illustrative dosage unit is an oral dosage unit such as tablets, pills, capsules, and the like. Similarly, the methods of administering a pharmaceutical composition to a patient is also intended to encompass the administration of the bulk composition and individual dosage units.

Suitable carriers, diluents, additives, and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), dimethylsulfoxide (DMSO), cremophor (e.g. CREMOPHOR EL®, BASF), and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an effective presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a labeled protein having the desired degree of purity may optionally be mixed with pharmaceutically acceptable diluents, carriers, excipients or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. The pharmaceutical formulation is preferably sterile. In particular, formulations to be used for in vivo administration must be sterile. Such sterilization is readily accomplished by filtration through sterile filtration membranes. The pharmaceutical formulation ordinarily can be stored as a solid composition, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being diagnosed or treated, the particular mammal being treated, the clinical condition of the individual patient, the cause of the disorder, the site of delivery of the agent, the method of administration, the scheduling of administration, and other factors known to medical practitioners. The "pharmaceutically effective amount" of the compound to be administered will be governed by such considerations, and is the minimum amount necessary to diagnose, prevent, ameliorate, or treat the disorder.

The initial pharmaceutically effective amount of the labeled protein administered orally or parenterally per dose will be in the range of about 0.01-1000 mg/kg, namely about 0.1 to 20 mg/kg of patient body weight per day, with the typical initial range of compound used being 0.3 to 15 mg/kg/day. The dose of the labeled protein and the dose of the chemotherapeutic agent to be administered may range for each from about 1 mg to about 1000 mg per unit dosage form, or from about 10 mg to about 100 mg per unit dosage form. The doses of labeled protein and the chemotherapeutic agent may administered in a ratio of about 1:50 to about 50:1 by weight, or in a ratio of about 1:10 to about 10:1 by weight.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, CREMOPHOR EL®, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences $18^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host and the particular mode of administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

Metabolites of Labeled Proteins

Also falling within the scope of this invention are the in vivo metabolic products of Labeled proteins described herein. Such products may result for example from the oxidation, reduction, hydrolysis, amidation, deamidation, esterification, deesterification, enzymatic cleavage, and the like, of the administered compound. Accordingly, the invention includes metabolites of labeled proteins, including compounds produced by a process comprising contacting a compound of this invention with a mammal for a period of time sufficient to yield a metabolic product thereof. The metabolite structures may be determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing labeled proteins useful for diagnosis of diseases and disorders is provided. In one embodiment, the kit comprises a container comprising a labeled protein. The kit may further comprise a label or package insert, on or associated with the container. The term "package insert" is used to refer to instructions customarily included in commercial packages of diagnostic products, that contain information about the usage, dosage, administration, contraindications and/or warnings concerning the use of such diagnostic products. Suitable containers include, for example, bottles, vials, syringes, blister pack, etc. The container may be formed from a variety of materials such as glass or plastic. The container may hold a labeled protein or a formulation thereof and may have a sterile access port (for example, the container may be an intravenous solution bag or a vial having a stopper pierceable by a hypodermic injection needle). At least one active agent in the composition is a labeled protein. In one embodiment, the label or package inserts indicates that the composition comprising a labeled protein can be used to diagnose a disorder resulting from abnormal cell growth. The label or package insert may also indicate that the composition can be used to diagnose other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes. The kit may further comprise directions for the administration of the pharmaceutical formulation of the labeled protein.

EXAMPLES

Unless otherwise noted, all reactions were run under an argon atmosphere in oven dried glassware. Reactions were stirred using Teflon-coated magnetic stirrer bars. Reactions were monitored using thin layer silica gel chromatography (TLC) using 0.25 mm silica gel 60F plates with fluorescent indicator from EMD Chemicals. Plates were visualized under UV light. Products were purified via preparative reverse phase chromatography with UV detection at 254 nm using a gradient of 5-50% water/ACN (0.1% formic acid) at 70 ml/min in 10 min; the column was a Phenomenex Gemini-NX 10u C18 110A, 100×30.00 mm.

Acetonitrile ($CH_3CN$) and trifluoroacetic acid (TFA) were purchased from EMD Chemicals. Acetic acid ($CH_3COOH$), ethyl isocyanoacetate, deuterated chloroform ($CDCl_3$), and N-chlorosuccinimide (NCS) were purchased from Alpha Aesar. Chloroform ($CHCl_3$) was purchased from Mallinckrodt. Methanol (MeOH) was purchased from J. T. Baker. 4-hydroxyphenylacetic acid was purchased from Sigma-Aldrich. Lithium hydroxide monohydrate ($LiOH.H_2O$) was purchased from Acros. Paraformaldehyde was purchased from TCI America. 2-Maleimidoethylamine hydrochloride was purchased from Oakwood Products (West Columbia, S.C.). 2-Aminoethyl-mono-amide-DOTA-tris(t-butyl ester) hydrobromide was purchased from Macrocyclics, Inc. (Dallas, Tex.).

NMR spectra were measured on either a Bruker 300 UltraShield™ ($^1H$ at 300 MHz, $^{13}C$ at 75 MHz) or a Bruker Avance II 400 ($^1H$ at 400 MHz, $^{13}C$ at 100 MHz) magnetic resonance spectrometer. 1H chemical shifts are reported relative to the residual solvent peak (chloroform=7.26 ppm) (Gottlieb, H. E.; Kotlyar, V.; Nudelman, A. (1997) *J. Org. Chem.*, 62:7512-7515) as follows: chemical shift ($\delta$), (multiplicity (s=singlet, br s=broad singlet, d=doublet, t=triplet, m=multiplet), integration). $^{13}C$ chemical shifts are reported relative to the residual deuterated solvent $^{13}C$ signals ($CDCl_3$=77.16 ppm). High resolution LC-MS was performed using an Agilent 1200 Series LC with PLRP-S, 1000 Å, column (50 mm×2.1 mm, Varian Inc., Palo Alto, Calif.) coupled to an Agilent 6220 Accurate-Mass TOF LC/MS mass spectrometer (Santa Clara, Calif.).

Reversed-phase radiochromatography was performed using an Agilent 1200 HPLC system coupled with a γ-RAM Model 4 radioactive detector (LabLogic, formerly IN/US, Brandon, Fla.) running Laura version 4 software. Size-exclusion radiochromatography was performed using an Agilent 1100 HPLC system coupled with a Raytest Gabi Star radioactive flow monitor (Wilmington, N.C.) running ChemStation software.

Example 1

Synthesis of tri-tert-butyl 2,2',2''-(10-(6-(2-(4-hydroxyphenyl)acetyl)-2,8,11-trioxo-12-oxa-3,6,9-triazatetradecyl)-1,4,7,10-tetraazacyclododecane-1,4,7-triyl)triacetate 2

To a 50-mL round bottom flask were added the following: tri-tert-butyl 2,2',2''-(10-(2-((2-aminoethyl)amino)-2-oxoethyl)-1,4,7,10-tetraazacyclododecane-1,4,7-triyl)triacetate 1 (0.5025 g, 0.724 mmol), paraformaldehyde (0.022 g, 0.724 mmol, 1 eq.), 4-hydroxyphenylacetic acid (0.110 g, 0.724 mmol, 1 eq.), and ethyl isocyanoacetate (0.081 g, 0.724 mmol, 1 eq.). The mixture was refluxed in 10 mL of MeOH under argon at 70° C. for 5 hours. After solvent removal in vacuo, purification was achieved by preparative reverse-phase HPLC (gradient from 100% 0.1% formic acid in water to 50% 0.1% formic acid in water/50% $CH_3CN$) to give 2 in 58.3% yield. $^1H$ NMR (300 MHz, $CDCl_3$) δ 8.87 (m, 1H), 8.48 (m, 1H), 7.03 (m, 2H), 6.81 (m, 2H), 6.34 (br s, 1H), 4.20-2.80 (m, 36H), 1.45 (s, 27H), 1.25 (t, 3H); $^{13}C$-NMR (75 MHz, $CDCl_3$) δ 173.66, 173.23, 170.18, 169.99, 169.77, 169.65, 167.67, 156.60, 156.40, 130.36, 130.04, 125.58, 116.03, 115.81, 82.11, 82.02, 81.98, 81.93, 61.34, 61.24, 56.61, 55.81, 55.48, 52.81, 52.54, 52.06, 50.79, 50.58, 49.99, 49.74, 49.25, 48.77, 47.08, 41.43, 39.59, 37.97, 28.13, 14.16.

Example 2

Synthesis of 2-(2-(2-(4-hydroxyphenyl)-N-(2-(2-(4,7,10-tris(2-(tert-butoxy)-2-oxoethyl)-1,4,7,10-tetraazacyclododecan-1-yl)acetamido)ethyl)acetamido)acetamido)acetic acid 3

To a 50-mL round bottom flask loaded with tri-tert-butyl 2,2',2''-(10-(6-(2-(4-hydroxyphenyl)acetyl)-2,8,11-trioxo-12-oxa-3,6,9-triazatetradecyl)-1,4,7,10-tetraazacyclododecane-1,4,7-triyl)triacetate 2 (0.260 g, 0.291 mmol) was added $LiOH.H_2O$ (0.018 g, 0.437 mmol, 1.5 eq.), 6 mL of EtOH, and 2 mL of $H_2O$. The reaction was stirred at room temperature for 12 hours. After solvent removal in vacuo, purification was achieved by preparative reverse-phase HPLC (gradient from 100% 0.1% formic acid in water to 50% 0.1% formic acid in water/50% $CH_3CN$) to give 3. 65.5% $^1$H-NMR (300 MHz, $CDCl_3$) δ 8.66 (m, 1H), 8.07 (m, 1H), 7.02 (m, 2H), 6.29 (m, 2H), 6.34 (br s, 1H), 4.20-2.80 (m, 34H), 1.44 (s, 27H); $^{13}$C-NMR (75 MHz, $CDCl_3$) δ 174.51, 174.14, 173.70, 173.45, 172.43, 169.80, 167.18, 156.59, 156.45, 130.43, 130.02, 125.93, 116.08, 115.89, 81.89, 81.85, 81.75, 56.42, 55.62, 52.76, 52.32, 51.61, 50.52, 49.67, 49.31, 49.25, 49.12, 47.69, 47.52, 43.54, 43.21, 40.37, 39.38, 38.07, 28.14.

Example 3

Synthesis of tri-tert-butyl 2,2',2''-(10-(14-(2,5-di-oxo-2,5-dihydro-1H-pyrrol-1-yl)-6-(2-(4-hydroxy-phenyl)acetyl)-2,8,11-trioxo-3,6,9,12-tetraazatetra-decyl)-1,4,7,10-tetraazacyclododecane-1,4,7-triyl) triacetate 4

To a 50-mL round bottom flask loaded with 2-(2-(2-(4-hydroxyphenyl)-N-(2-(2-(4,7,10-tris(2-(tert-butoxy)-2-oxo-ethyl)-1,4,7,10-tetraazacyclododecan-1-yl)acetamido)ethyl) acetamido)acetamido)acetic acid 3 (0.113 g, 0.131 mmol) was added 1-ethyl-3-(3-dimethylaminopropyl)carbodiimide (0.038 g, 0.198 mmol, 1.5 eq.) and 2-maleimidoethylamine-.HCl (0.035 g, 0.198 mmol, 1.5 eq.). The mixture was dissolved in 10 mL of $CH_3CN$ and stirred for 12 hours at room temperature. After solvent removal in vacuo, purification was achieved by preparative reverse-phase HPLC (gradient from 100% 0.1% formic acid in water to 50% 0.1% formic acid in water/50% $CH_3CN$) to give 4. $^1$H-NMR (300 MHz, $CDCl_3$) δ 9.02 (m, 1H), 8.07 (m, 1H), 7.01 (m, 2H), 6.79 (m, 2H), 6.65 (s, $^1$H), 4.23-2.80 (m, 34H), 1.45 (s, 27H); $^{13}$C-NMR (75 MHz, $CDCl_3$) δ 173.67, 173.43, 171.04, 170.33, 170.26, 170.08, 169.94, 169.86, 168.64, 156.55, 156.47, 134.16, 130.33, 130.06, 125.57, 125.09, 115.95, 115.84, 81.93, 81.87, 81.81, 81.70, 56.63, 56.08, 55.90, 53.12, 52.01, 50.95, 49.79, 49.41, 49.39, 47.22, 43.44, 43.07, 39.58, 39.15, 38.25, 38.10, 37.74, 37.34, 28.17.

Example 4

Synthesis of tert-butyl 2,2',2''-(10-(14-(2,5-dioxo-2,5-dihydro-1H-pyrrol-1-yl)-6-(2-(4-hydroxy-3-iodo-phenyl)acetyl)-2,8,11-trioxo-3,6,9,12-tetraazatetra-decyl)-1,4,7,10-tetraazacyclododecane-1,4,7-triyl) triacetate 5

Figure 4:
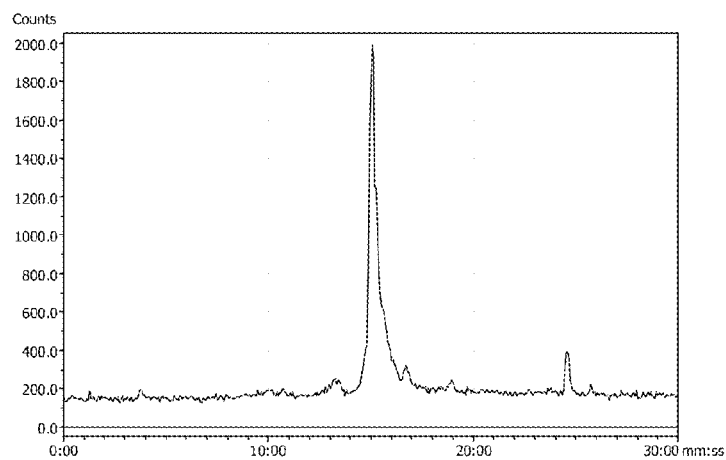
FIG. 4 shows reverse-phase radiochromatogram of 5

A 1.5-mg quantity of 4 was dissolved in 1.5 mL of chloroform, and the resulting solution was serially diluted. To 0.5 mL of a 0.01 mg/mL solution of 4 in chloroform was added 10 μL of a 25 mg/mL solution of N-chlorosuccinimide in chloroform followed by 3 μL of $Na^{125}I$ (~1.1 mCi) in aqueous 0.1 N NaOH (Perkin Elmer). After briefly mixing in a glass scintillation vial, the vial lid was removed, and the reaction was mixed continuously at 350 rpm for 10 minutes on an automated mixer, THERMOMIXER® (Eppendorf Corp.) without heating. A gentle stream of nitrogen gas was used to evaporate residual solvent, and the residue was reconstituted in 3 mL of aqueous 0.1% acetic acid using a plastic syringe. This solution was loaded onto a primed C-18 Sep-Pak Plus (Waters), rinsed with two 5-mL aliquots of the acidic water, flushed with a column volume of air, and eluted in 3 mL of acetonitrile. The resulting product 5 (275 μCi, 24% radiochemical yield) was analyzed by reversed phase chromatography (FIG. 4).

Example 5

Synthesis of 2,2',2''-(10-(14-(2,5-dioxo-2,5-dihydro-1H-pyrrol-1-yl)-6-(2-(4-hydroxy-3-iodophenyl) acetyl)-2,8,11-trioxo-3,6,9,12-tetraazatetradecyl)-1,4,7,10-tetraazacyclododecane-1,4,7-triyl)triacetic acid 6

After solvent removal by rotary evaporation, a 0.5 mL quantity of 95% trifluoroacetic acid/5% water was added followed by magnetic stirring for 1 hour to form 6, also referred to as [$^{125}$I] HIP-DOTA, by deprotection of the tert-butyl ester groups. Complete removal of acid by rotary evaporation was facilitated by successive additions of toluene in 250 μL aliquots. To the residue, still in a glass scintillation vial, was added 50 μL of phosphate-buffered saline, pH 7.4 (PBS). After a brief vortex, a pH strip was used to ensure that the pH was in the range of 6.5-7.5.

Example 6

Conjugation of Radioiodine-Labeling Reagent HIP-DOTA 6 to Thio-Trastuzumab

Figure 5:
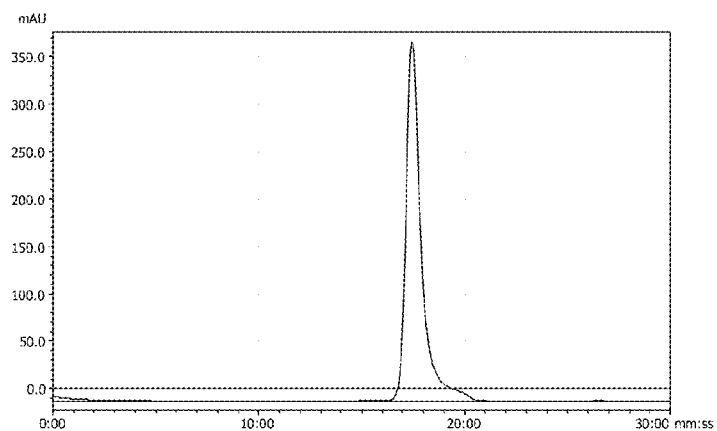
FIG. 5 shows size exclusion UV chromatogram of non-radioactive trastuzumab

The construction, expression, and purification of THIO-MAB with Cys substitution at Ala$^{114}$ (Kabat numbering) in heavy chain was described previously (Junutula J R, et al "Site-specific conjugation of a cytotoxic drug to an antibody improves the therapeutic index" (2008) Nat Biotechnol 26:925-32). The isolated thio-trastuzumab was prepared for conjugation by a reduction and re-oxidation procedure to remove disulfide adducts bound to Cys$^{114}$. FIG. 5 shows Size exclusion UV chromatogram of non-radioactive trastuzumab Trastuzumab was reduced for 24 h by treatment with a 40-fold molar excess of DTT and 2 mM EDTA in 88 mM Tris buffer pH 7.5. To remove DTT prior to re-oxidation, the thio-trastuzumab solution was adjusted to pH 5 by the addition of 10 mM sodium succinate buffer. The solution was then loaded on an ion exchange column (Hi-Trap SP FF, GE Healthcare) that had been sterilized and equilibrated with 10 mM sodium succinate buffer pH 5. The column was washed with 10 mM sodium succinate buffer (10 mL) and the thio-trastuzumab was then eluted with 3 mL of 50 mM Tris, 150 mM NaCl buffer with pH 7.5. Thio-trastuzumab re-oxidization was achieved by treatment with a 25-fold molar excess of dehydroascorbic acid DHA (100 mM in N,N-dimethylacetamide (DMA)) in 75 mM Tris, 150 mM NaCl pH 7.5 buffer at 25° C. for 3.5 h.

Figure 6:
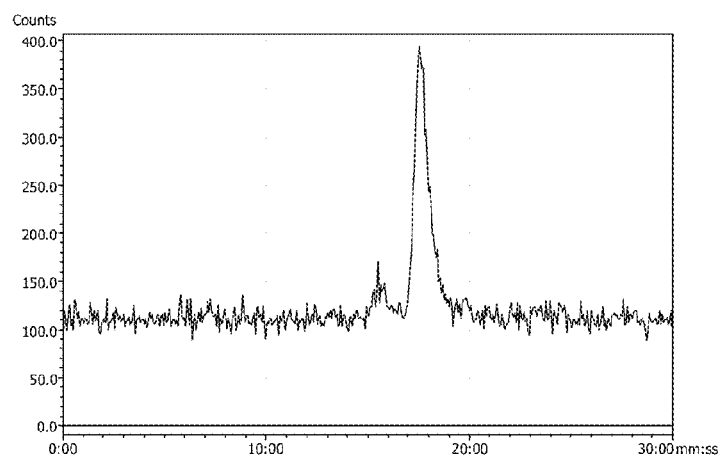
FIG. 6 shows size exclusion radiochromatogram of $^{125}$I-6-trastuzumab

A 50-μL aliquot of 9.7 mg/mL deblocked thio-trastuzumab (HC A118C; Genentech, South San Francisco, Calif.) was quickly added to the phosphate solution of 2,2',2''-(10-(14-(2,5-dioxo-2,5-dihydro-1H-pyrrol-1-yl)-6-(2-(4-hydroxy-3-iodophenyl)acetyl)-2,8,11-trioxo-3,6,9,12-tetraazatetradecyl)-1,4,7,10-tetraazacyclododecane-1,4,7-triyl) triacetic acid 6, followed by an additional 150 μL of PBS. This cysteine-engineered antibody (ThioMab) was engineered such that the alanine residues at 118 (114 Kabat) of each heavy chain were mutated to cysteine (Junutula, J. R., et al (2008) Nat Biotechnol., 26:925-932). If necessary, the final pH was carefully adjusted to 7.5 by addition of 50 mM borate buffer pH 8.5 in 10 μL increments. The reaction mixture was constantly mixed at 350 rpm for 1 h, followed by addition of a ten-fold molar excess of iodoacetic acid to quench the remaining free thiols. The desired radioimmunoconjugate (108.2 μCi, 39% conjugation yield) was purified using a PBS-equilibrated NAPS desalting col column (GE Healthcare, Life Sciences) and analyzed by size exclusion chromatography. FIG. 6 shows size exclusion radiochromatogram of $^{125}$I-6-trastuzumab.

Trastuzumab was also radiolabeled by traditional means, through its tyrosine residues, with $^{125}$I (862 μCi, 68% radiochemical yield) by the indirect Chizzonite method (Chizzonite, R., et al (1991) J Immunol., 147:1548) with modifications as previously described (Pastuskovas, C. V., et al (2012) Mol Cancer Ther., 11:752). Trastuzumab was conjugated to DOTA and radiolabeled with $^{111}$In (958 μCi, 71% radiochemical yield).

Example 7

Biodistribution and Pharmacokinetics

All animal studies were conducted in accordance with the guidelines of the American Association for Accreditation of Laboratory Animal Care and the Genentech Institutional Animal Care and Use Committee. C.B-17 Icr SCID (severe combined immunodeficient; Inbred) female mice (Charles River Laboratories), weighing between 20 to 25 g were inoculated in the right mammary fat pad with approximately 3 million KPL-4 cells in a 50:50 suspension of Hanks' Buffered Salt Solution (Invitrogen) and MATRIGEL® (BD Biosciences) in at most 0.2 mL/mouse. When mean tumor volume reached at least 250 mm$^3$, mice received a single bolus intravenous injection via the tail vein containing $^{111}$In-trastuzumab (5 μCi) together with either $^{125}$I-trastuzumab (5 μCi) or $^{125}$I-6-trastuzumab (5 μCi). To minimize thyroid sequestration of $^{125}$I, 100 μL of 30 mg/mL of sodium iodide was intraperitoneally administered 1 and 24 hours before dosing. Blood samples were collected at 5 min and 24 hours post-injection via retroorbital bleed, and terminal tissue harvest was performed at 72 hours post-injection. Terminally collected samples included liver, spleen, kidneys, lungs, intestine (ileum), muscle (gastrocnemius), blood, and tumor. Tissues were counted for radioactivity using a 2480 Wizard$^2$ automatic gamma counter (Perkin Elmer). Counts per minute values were used to calculate the percent of injected dose per gram of tissue (% ID/g) (Pastuskovas, C. V., et al, (2012) *Mol Cancer Ther.,* 11, 752).

Whole-body autoradiographic imaging at 3 days post-injection of the HC-A114C, LC-V205C and FC-S396C variants of thio-trastuzumab indicated relative degrees of tracer residualization in KPL-4 tumor-bearing mice following intravenous administration of trastuzumab radiolabeled by 5 different methods, including the three ThioMab variants of 125I-6 trastuzumab. Post-mortem cryosection images from a sagittal perspective were acquired from the same mice whose live, non-invasive images appear in FIG. 15. Phosphorimages and digital photographs showed distribution in thyroid (TH) and heart tissues (H) for each mouse in the mid-line plane.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

We claim:
1. A radiohalogen-labeling reagent having the structure:

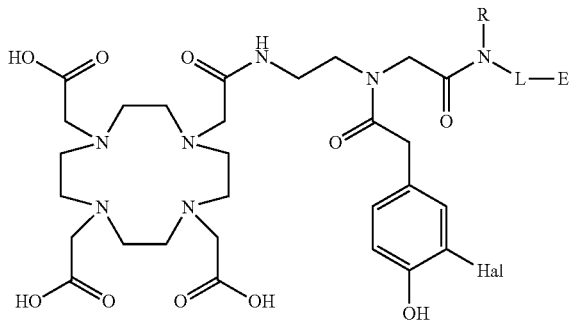

wherein
Hal is a radiohalide isotope selected from $^{123}$I, $^{124}$I, $^{125}$I, $^{131}$I, and $^{211}$At;
L is a linker selected from —(C$_1$-C$_{12}$ alkylene)-C(O)NR—(C$_1$-C$_{12}$ alkylene)-, —(C$_1$-C$_{12}$ alkylene)-C(O)NR—(C$_1$-C$_{12}$ alkylene)O—, —(C$_1$-C$_{12}$ alkylene)-C(O)NR—(C$_1$-C$_{12}$ alkylene)-C(O)NR—(C$_1$-C$_{12}$ alkylene)-C(O)CH$_2$—, —(C$_1$-C$_{12}$ alkylene)-C(O)N(R)—, —(C$_1$-C$_{12}$ alkylene)-C(O)NR—(C$_2$-C$_8$ alkenylene)-, —(C$_1$-C$_{12}$ alkylene)-C(O)NR—(C$_2$-C$_8$ alkynylene)-, —(C$_1$-C$_{12}$ alkylene)-C(O)NR(CH$_2$CH$_2$O)$_n$—, —(C$_1$-C$_{12}$ alkylene)-C(O)—, —(C$_1$-C$_{12}$ alkylene)-C(O)NR(CH$_2$CH$_2$O)$_n$CH$_2$C(O)—, and —(C$_1$-C$_{12}$ alkylene)-C(O)NR(CH$_2$CH$_2$O)$_n$CH$_2$—,
where n is 1 to 6, R is H, C$_1$-C$_{12}$ alkyl, or C$_6$-C$_{20}$ aryl, and alkylene, alkenylene, alkynylene, alkyl, and aryl are optionally substituted with one or more groups selected from F, Cl, Br, I, —CH$_3$, —CH$_2$CH$_3$, —CH(CH$_3$)$_2$, —CH$_2$CH(CH$_3$)$_2$, —CH$_2$NH$_2$, —CH$_2$CH$_2$NH$_2$, —CH$_2$CHCH$_2$NH$_2$, —CH$_2$CH(CH$_3$)NH$_2$, —CH$_2$OH, —CH$_2$OCH$_3$, —CH$_2$CH$_2$OH, —CH$_2$CH$_2$OCH$_3$, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, =O, —OH, —OCH$_3$, —OP(O)$_3$, —S(O)$_2$N(CH$_3$)$_2$, —S(O)$_3$, —SCH$_3$, and —S(O)$_2$CH$_3$; and
E is a reactive functional group selected from maleimide, thiol, amino, bromide, bromoacetamido, p-toluenesulfonate, iodide, hydroxyl, carboxyl, aldehyde, pyridyl disulfide, N-hydroxysuccinimide, azido, isocyanato, isothiocyanato, and phosphoramidite.

2. The radiohalogen-labeling reagent of claim 1 wherein E is maleimide.

3. The radiohalogen-labeling reagent of claim 2 having the formula:

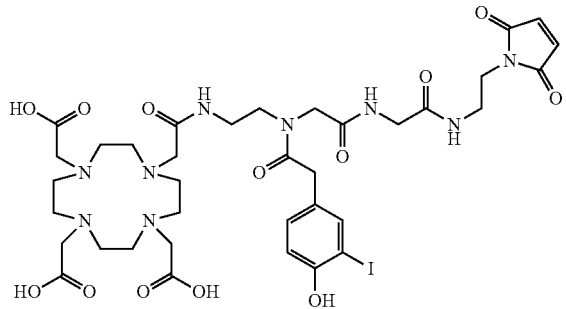

where I is an iodine isotope selected from $^{123}$I, $^{124}$I, $^{125}$I, and $^{131}$I.

4. The radiohalogen-labeling reagent of claim 1 wherein E is N-hydroxysuccinimide.

5. The radiohalogen-labeling reagent of claim 4 having the formula:

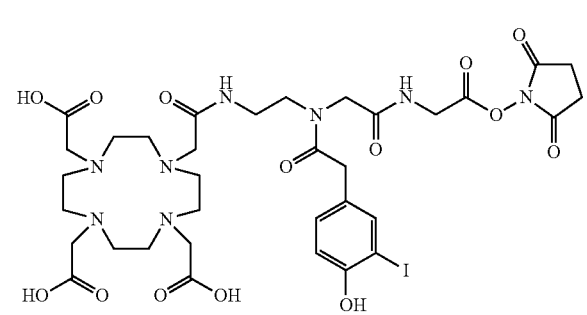

where I is an iodine isotope selected from $^{123}$I, $^{124}$I, $^{125}$I, and $^{131}$I.

* * * * *